United States Patent
Tulkis

(10) Patent No.: US 11,202,713 B2
(45) Date of Patent: Dec. 21, 2021

(54) MODULAR FEMORAL TRIALING SYSTEM HAVING ADJUSTABLE HEIGHT

(71) Applicant: Howmedica Osteonics Corp., Mahwah, NJ (US)

(72) Inventor: Peter Tulkis, Paramus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 236 days.

(21) Appl. No.: 16/282,995

(22) Filed: Feb. 22, 2019

(65) Prior Publication Data
US 2020/0268529 A1    Aug. 27, 2020

(51) Int. Cl.
*A61F 2/32*    (2006.01)
*A61F 2/46*    (2006.01)
(Continued)

(52) U.S. Cl.
CPC .......... *A61F 2/4684* (2013.01); *A61F 2/3662* (2013.01); *A61F 2/367* (2013.01); *A61F 2/3676* (2013.01); *A61F 2002/305* (2013.01); *A61F 2002/3055* (2013.01); *A61F 2002/30168* (2013.01); *A61F 2002/30362* (2013.01); *A61F 2002/30364* (2013.01);
(Continued)

(58) Field of Classification Search
CPC .......... A61F 2/4684; A61F 2002/30604; A61F 2002/30616; A61F 2/36–2002/3698; A61F 2002/30364; A61F 2002/30518; A61F 2002/3039–30395; A61F 2002/30494; A61F 2002/305; A61F 2002/30362–30369; A61F 2002/30487
See application file for complete search history.

(56) References Cited

U.S. PATENT DOCUMENTS 4,135,517 A * 1/1979 Reale .................... A61F 2/4684
                                                                  606/86 R
5,601,567 A    2/1997 Swajger et al.
(Continued)

FOREIGN PATENT DOCUMENTS

DE    102008030260 A1 * 12/2009 ........... A61F 2/4684

OTHER PUBLICATIONS

Machine translation of DE102008030260, pp. 1-22, accessed Mar. 25, 2021. (Year: 2021).*

*Primary Examiner* — Rebecca S Preston
(74) *Attorney, Agent, or Firm* — Lerner, David, Littenberg, Krumholz & Mentlik, LLP

(57) ABSTRACT

An assembly for attachment to a first implant component has a size and shape of a second implant component to be implanted together with the first implant component. The assembly includes a first body including a plug having a projection, and a second body including a recess having an internal surface defining at least one indentation. In a temporary configuration, when the plug is disposed within the recess and the projection is disposed at least partially within one of the at least one indentations, the first and second bodies are removably connected such that the first and second bodies are prevented from separating. A method of assembling the assembly includes removably connecting the plug of the first body into the recess of the second body by locating the projection within an indentation, such that the bodies are prevented from separating, and positioning the assembly on the first implant component.

18 Claims, 16 Drawing Sheets

(51) Int. Cl.
*A61F 2/36* (2006.01)
*A61F 2/30* (2006.01)

(52) U.S. Cl.
CPC .............. *A61F 2002/30367* (2013.01); *A61F 2002/30433* (2013.01); *A61F 2002/30476* (2013.01); *A61F 2002/30518* (2013.01); *A61F 2002/30553* (2013.01); *A61F 2002/30604* (2013.01); *A61F 2002/30616* (2013.01); *A61F 2002/3621* (2013.01); *A61F 2002/3627* (2013.01); *A61F 2002/3652* (2013.01)

(56) References Cited

U.S. PATENT DOCUMENTS

| | | | |
|---|---|---|---|
| 5,702,480 | A | 12/1997 | Kropf et al. |
| 5,876,459 | A | 3/1999 | Powell |
| 5,906,644 | A | 5/1999 | Powell |
| 6,319,286 | B1 | 11/2001 | Fernandez et al. |
| 6,432,110 | B1 | 8/2002 | Richelsoph |
| 6,702,854 | B1 | 3/2004 | Cheal et al. |
| 7,235,106 | B2 | 6/2007 | Daniels et al. |
| 7,951,205 | B2 | 5/2011 | McCleary et al. |
| 8,252,002 | B2 | 8/2012 | Huff et al. |
| 8,758,446 | B2 | 6/2014 | Smith |
| 9,597,203 | B2 | 3/2017 | Emerick et al. |
| 2003/0204262 | A1 | 10/2003 | Ferguson et al. |
| 2003/0204267 | A1* | 10/2003 | Hazebrouck .......... A61F 2/3854 623/23.39 |
| 2003/0204269 | A1* | 10/2003 | Gerbec .................. A61F 2/367 623/23.47 |
| 2004/0064190 | A1 | 4/2004 | Ball et al. |
| 2009/0048682 | A1* | 2/2009 | Choi ........................ A61F 2/36 623/23.44 |
| 2010/0292806 | A1 | 11/2010 | Daniels et al. |
| 2011/0224798 | A1 | 9/2011 | Caillouette et al. |
| 2016/0158028 | A1 | 6/2016 | Borries et al. |
| 2016/0278945 | A1 | 9/2016 | Emerick et al. |
| 2019/0117412 | A1 | 4/2019 | Zimmerman et al. |

\* cited by examiner

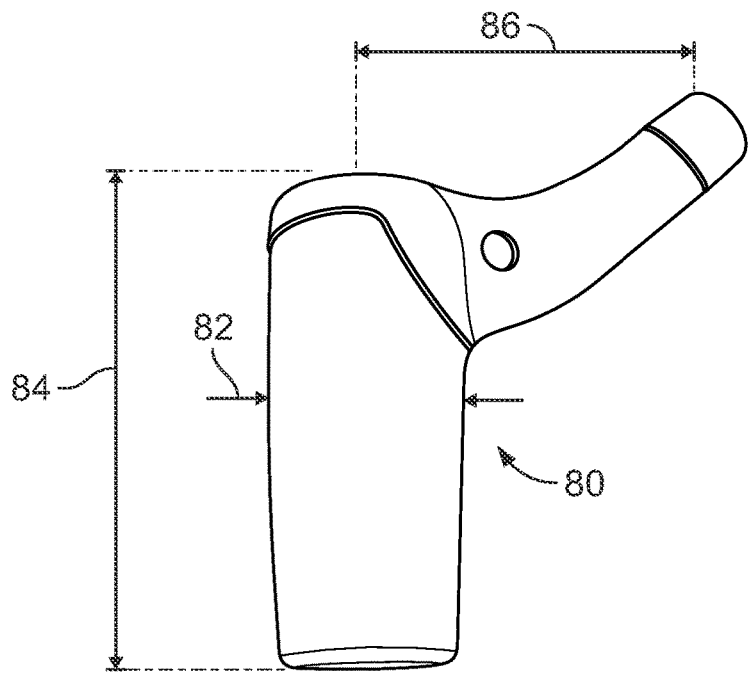
FIG. 1
(Prior Art)
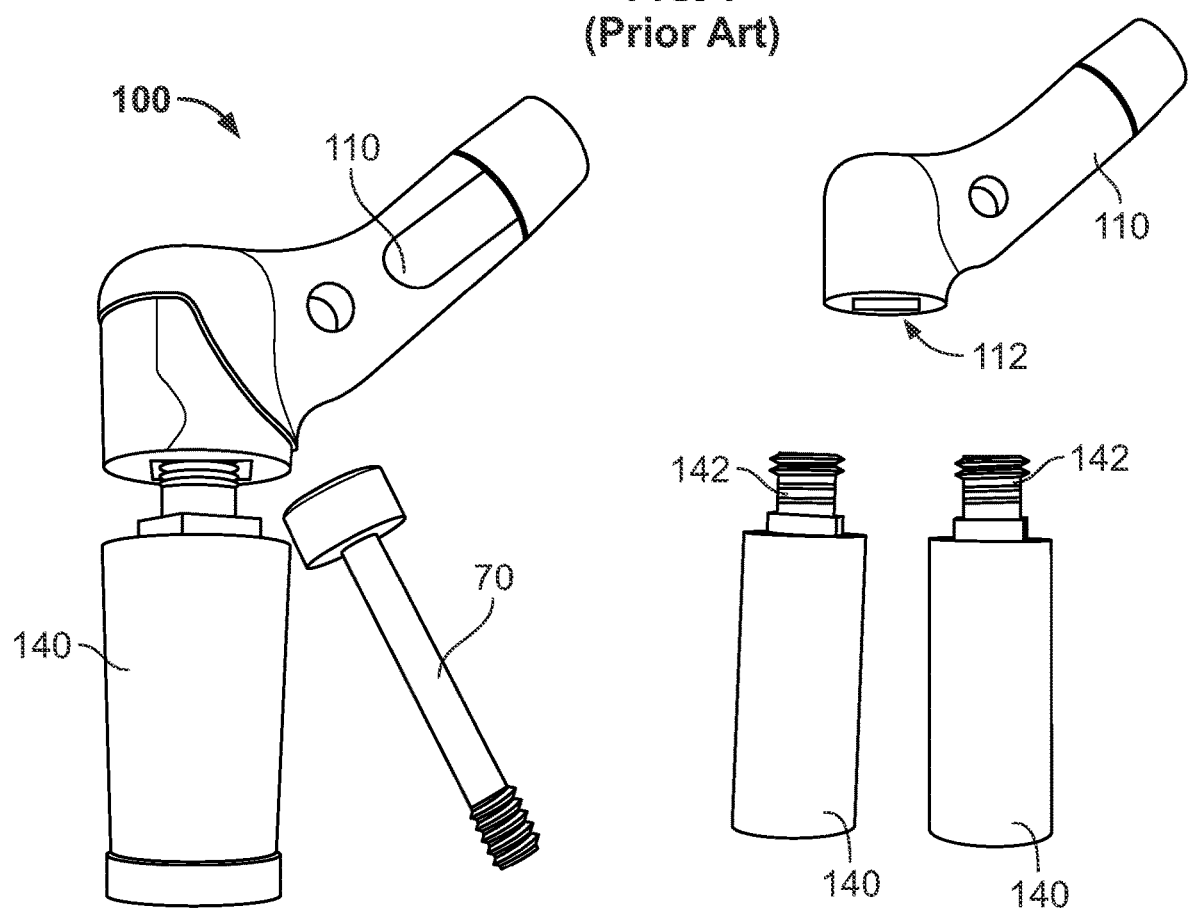
FIG. 2
FIG. 3

| Length (mm) | Cone Body Diameter | | | | | | | |
|---|---|---|---|---|---|---|---|---|
| | 17mm | 19mm | 21mm | 23mm | 25mm | 27mm | 29mm | 31mm |
| 50 | 2X | - | - | - | - | - | - | - |
| 60 | 2X | 2X | 2X | 2X | - | - | - | - |
| STD (70) | 2X | 2X | 2X | 2X | 1X | 1X | 1X | 1X |
| +10 (80) | - | 2X | 2X | 2X | 1X | 1X | 1X | 1X |
| +20 (90) | - | 1X | 1X | 1X | 1X | 1X | 1X | 1X |
| +30 (100) | - | 1X | 1X | 1X | 1X | 1X | 1X | 1X |
| Offset (mm) | 30 34 | 34 38 | 36 40 | 40 44 | 44 | 44 | 44 | 44 |

FIG. 31

MODULAR FEMORAL TRIALING SYSTEM HAVING ADJUSTABLE HEIGHT

BACKGROUND OF THE INVENTION

The present disclosure relates to trialing systems for prosthetic implants. More particularly, the present disclosure relates to modular trialing systems including components that can be temporarily and fixedly connected during a trialing procedure and methods of conducting a trialing procedure using such systems.

In current femoral revision systems, a proximal body and distal stem are implanted into the patient. In order to properly analyze the fit of the final implant, a trial of the proximal body is attached to the distal stem. The joint is then reduced and evaluated. If another size implant would better fit the anatomy of the patient, the trial of the proximal body is replaced with a differently sized trial, and the process is repeated. Once the proper fit is found, a permanent proximal body is located that corresponds to the proper trial.

Current trials corresponding to the proximal body are one-piece, monolithic structures, such as the proximal body 80 shown in FIG. 1 having a trunk and a femoral neck. The femoral neck has a conical proximal surface at its terminal end for connecting with a trial femoral head. The conical proximal surface defines a center point corresponding to that of an implanted femoral head. Each trial corresponds to just one permanent implant, and vice versa. Thus, a tray of trials equaling the number of unique permanent implants is required to perform each surgical procedure. Trials are typically the most expensive components in the trialing set, accounting for approximately 40% of the total cost of the system. Accordingly, New sizes of implants increase set cost and increase tray size.

As shown in FIG. 1, each proximal body 80 is unique in one or more parameters, including a maximum outer diameter 82 of its trunk, a maximum height 84 of its trunk, and an offset distance 86 measured perpendicularly from the axis of the trunk to the center point of the conical proximal surface of the femoral neck, which coincides with a center point of the corresponding femoral head.

A modular trialing system is needed that improves the efficiency of trialing procedures and reduces the cost and number of components in a trialing set.

BRIEF SUMMARY OF THE INVENTION

A first aspect of the present invention is an assembly for attachment to a first implant component, the assembly having a size and shape of a second implant component to be implanted together with the first implant component, including a first body, and a second body removably connected to the first body, wherein in a temporary configuration, the first and second bodies are prevented from separating while the first and second bodies permit relative movement therebetween.

In accordance with other embodiments of the first aspect, in a fixed configuration, the first and second bodies may be prevented from separating while relative movement is not permitted between the first and second bodies. The assembly may further include a locking screw, and in the fixed configuration, the locking screw may be secured through the first body and the second body and into a portion of the first implant component. The first and second bodies may be connectable along an axis and may each define lumens aligned with the axis in which the locking screw can be disposed. The first and second bodies may be connectable along an axis, and the relative movement may be translational along and/or rotational about the axis. A modular kit may include a plurality of the first bodies as defined above each having a different size or shape, and a plurality of the second bodies as defined above each having a different size or shape. The kit may further include a permanent implant component having the same dimensions as the assembly.

The first body may define a recess and the second body may include a protrusion insertable into the recess. The protrusion may include a terminal end and an external surface defining a non-threaded portion and defining a threaded portion that is located closer to the terminal end of the protrusion than its non-threaded portion is, and the recess may include a terminal end and an internal surface defining a non-threaded portion and defining a threaded portion that is located closer to the terminal end of the recess than its non-threaded portion is. When the assembly is in the temporary configuration, the entire threaded portion of the protrusion may be located within the recess past the threaded portion of the recess. The threaded portions of the protrusion and the recess may engage one another as the protrusion is inserted into the recess. The protrusion may include an anti-rotation portion at a base end opposite its terminal end that has a non-circular cross section, and the recess may include an anti-rotation portion at its terminal end that has a non-circular cross section. The non-circular cross sections may be square cross sections.

When assembled together, the first and second bodies may correspond to a cone body of a femoral hip assembly as the second implant component. The first body may define a femoral neck and an upper portion of a trunk of the cone body, and the second body may define a lower portion of the trunk of the cone body. The upper and lower portions of the trunk of the cone body may be connectable along a first axis, and the femoral neck of the first body may extend along a second axis that is angled with respect to the axis. The trunk may define a maximum outer diameter, the second body may define a maximum height, and the femoral neck may have a conical proximal surface for connecting with a femoral head, the conical proximal surface defining a center point of the proximal neck, and wherein the first body defines an offset distance measured perpendicularly from the axis to the center point. A modular femoral trialing kit may include a plurality of the first bodies as defined above each having a different size or shape, and a plurality of the second bodies as defined above each having a different size or shape. The maximum outer diameter of the trunk may be provided in sizes of 17, 19, 21, 23, 25, 27, 29, and 31 mm. The maximum height of the second body may be provided in sizes of 50, 60, 70, 80, 90, and 100 mm. The offset distance of the femoral neck may be provided in sizes of 30, 34, 36, 38, 40, and 44 mm. The kit may further include a locking screw for securing the first body to the second body on a portion of an implant.

A second aspect of the present invention is a method of assembling an assembly for attachment to a first implant component, the assembly having a size and shape of a second implant component to be implanted together with the first implant component, including the steps of removably connecting a first body of the assembly to a second body of the assembly, such that the first and second bodies are prevented from separating while permitting relative movement therebetween, and positioning the assembly on the first implant component.

In accordance with other embodiments of the second aspect, the method may further include the step of fixedly connecting the first body to the second body together by securing the assembly to the first implant component to prevent relative movement between the first and second bodies. The step of fixedly connecting may include securing a locking screw through the first body and the second body and into a portion of the first implant component. The method may further include the step of assessing the biomechanics of a joint with the implanted assembly. The step of removably connecting may include permitting relative movement translationally along and/or rotationally about an axis along which the first and second bodies are connectable.

The step of removably connecting may include inserting a protrusion of the second body into a recess defined by the first body. The step of removably connecting may include threading a threaded portion defined by an external surface of the protrusion into engagement with a threaded portion defined by an internal surface of the recess, and further threading the threaded portion of the protrusion until the entire threaded portion of the protrusion is located within the recess past the threaded portion of the recess. The method may further include the step of fixedly connecting the first body to the second body together by securing the assembly to the first implant component to prevent relative movement between the first and second bodies, including preventing rotation of the first body with respect to the second body by engaging an anti-rotation portion at a base end of the protrusion that has a non-circular cross section with an anti-rotation portion at a terminal end of the recess that has a non-circular cross section.

The method may further include the step of selecting the second implant component having the same dimensions as the assembly. The method may further include the steps of selecting the first body from a kit including a plurality of the first bodies each having a different size or shape, and selecting the second body from the kit including a plurality of the second bodies each having a different size or shape.

A third aspect of the present invention is an assembly for attachment to a first implant component, the assembly having a size and shape of a second implant component to be implanted together with the first implant component, including a first body defining a recess, the recess having an internal surface defining an annular groove, a second body including a protrusion insertable into the recess, the protrusion having an external surface defining an annular groove, and a split ring, wherein, when the split ring is disposed at least partially within the annular grooves of the protrusion and the recess, the first and second bodies are removably connected such that the first and second bodies are prevented from separating.

In accordance with other embodiments of the third aspect, the assembly may further include a locking screw configured to be secured through the first body and the second body and into a portion of the first implant component. The first and second bodies may be connectable along an axis and may each define lumens aligned with the axis in which the locking screw can be disposed. Tabs on one of the recess and the protrusion may be disposed within indents on the other of the recess and the protrusion to prevent relative rotation between the first and second bodies. A modular kit may include a plurality of the first bodies as defined above each having a different size or shape, and a plurality of the second bodies as defined above each having a different size or shape. The kit may further include a permanent implant component having the same dimensions as the assembly.

When assembled together, the first and second bodies may correspond to a cone body of a femoral hip assembly as the second implant component. The first body may define a femoral neck and an upper portion of a trunk of the cone body, and the second body may define a lower portion of the trunk of the cone body. The upper and lower portions of the trunk of the cone body may connectable along a first axis, and the femoral neck of the first body may extend along a second axis that is angled with respect to the axis. The trunk may define a maximum outer diameter, the second body may define a maximum height, and the femoral neck may have a conical proximal surface for connecting with a femoral head, the conical proximal surface defining a center point of the proximal neck, and wherein the first body defines an offset distance measured perpendicularly from the axis to the center point. A modular femoral trialing kit may include a plurality of the first bodies as defined above each having a different size or shape, and a plurality of the second bodies as defined above each having a different size or shape. The maximum outer diameter of the trunk may be provided in sizes of 17, 19, 21, 23, 25, 27, 29, and 31 mm. The maximum height of the second body may be provided in sizes of 50, 60, 70, 80, 90, and 100 mm. The offset distance of the femoral neck may be provided in sizes of 30, 34, 36, 38, 40, and 44 mm. The kit may further include a locking screw for securing the first body to the second body on a portion of an implant.

A fourth aspect of the present invention is a method of assembling an assembly for attachment to a first implant component, the assembly having a size and shape of a second implant component to be implanted together with the first implant component, including the steps of removably connecting a protrusion of a second body of the assembly into a recess defined by a first body of the assembly to move a split ring at least partially into an annular groove defined in an external surface of the protrusion and at least partially into an annular groove defined in an internal surface of the recess, such that the first and second bodies are prevented from separating, and positioning the assembly on the first implant component.

In accordance with other embodiments of the fourth aspect, the method may further include the step of fixedly connecting the first body to the second body together by securing a locking screw through the first body and the second body and into a portion of the first implant component. The method may further include the step of assessing the biomechanics of a joint with the implanted assembly. The step of removably connecting may further include inserting tabs on one of the recess and the protrusion within indents on the other of the recess and the protrusion to prevent relative rotation between the first and second bodies. The method may further include the step of selecting the second implant component having the same dimensions as the assembly. The method may further include the steps of selecting the first body from a kit including a plurality of the first bodies each having a different size or shape, and selecting the second body from the kit including a plurality of the second bodies each having a different size or shape.

A first aspect of the present invention is an assembly for attachment to a first implant component, the assembly having a size and shape of a second implant component to be implanted together with the first implant component, including a first body and a second body removably connectable to the first body, wherein in a temporary configuration, when the second body is removably connected to the first body, the first and second bodies are prevented from separating while the first and second bodies permit relative movement therebetween.

In accordance with other embodiments of the first aspect, in a fixed configuration, the first and second bodies may be prevented from separating while relative movement is not permitted between the first and second bodies. The assembly may further include a locking screw, and in the fixed configuration, the locking screw may be secured through the first body and the second body and into a portion of the first implant component. The first and second bodies may be connectable along an axis and each may define lumens aligned with the axis in which the locking screw can be disposed. The first and second bodies may be connectable along an axis, and the relative movement may be translational along the axis and/or rotational about the axis.

The first body may define a recess and the second body may include a protrusion insertable into the recess. The protrusion may include a terminal end and an external surface defining a non-threaded portion and defining a threaded portion that is located closer to the terminal end of the protrusion than its non-threaded portion is, and the recess may include a terminal end and an internal surface defining a non-threaded portion and defining a threaded portion that is located closer to the terminal end of the recess than its non-threaded portion is. When the assembly is in the temporary configuration, the entire threaded portion of the protrusion may be located within the recess past the threaded portion of the recess. The threaded portions of the protrusion and the recess may engage one another as the protrusion is inserted into the recess. The protrusion may include an anti-rotation portion at a base end opposite its terminal end that has a non-circular cross section, and the recess may include an anti-rotation portion at its terminal end that has a non-circular cross section. The non-circular cross sections may be square cross sections.

When assembled together, the first and second bodies may correspond to a cone body of a femoral hip assembly as the second implant component. The first body may define a femoral neck and an upper portion of a trunk of the cone body, and the second body may define a lower portion of the trunk of the cone body. The upper and lower portions of the trunk of the cone body may be connectable along a first axis, and the femoral neck of the first body may extend along a second axis that is angled with respect to the first axis. The trunk may define a maximum outer diameter and a maximum height, and the femoral neck may have a conical proximal surface for connecting with a femoral head, the conical proximal surface defining a center point of the proximal neck, and wherein the first body defines an offset distance measured perpendicularly from the first axis to the center point.

A modular femoral trialing kit may include a plurality of the first bodies according to the above, each having a different size or shape, and a plurality of the second bodies according to the above, each having a different size or shape. The maximum outer diameter of the trunk may be provided in sizes of 17, 19, 21, 23, 25, 27, 29, and 31 mm, or in other sizes. The maximum height of the trunk may be provided in sizes of 50, 60, 70, 80, 90, and 100 mm, or in other sizes. The offset distance of the femoral neck may be provided in sizes of 30, 34, 36, 38, 40, and 44 mm, or in other sizes. The kit may further include a locking screw for securing the first body to the second body on a portion of an implant.

A second aspect of the present invention is a method of assembling an assembly for attachment to a first implant component, the assembly having a size and shape of a second implant component to be implanted together with the first implant component, including the steps of removably connecting a first body of the assembly to a second body of the assembly, such that the first and second bodies are prevented from separating while permitting relative movement therebetween, and positioning the assembly on the first implant component.

In accordance with other embodiments of the second aspect, the method may further include the step of fixedly connecting the first body to the second body together by securing the assembly to the first implant component to prevent relative movement between the first and second bodies. The step of fixedly connecting may include securing a locking screw through the first body and the second body and into a portion of the first implant component. The method may further include the step of assessing the biomechanics of a joint with the implanted assembly.

The step of removably connecting may include permitting relative movement translationally along an axis along which the first and second bodies are connectable. The step of removably connecting may include permitting relative movement rotationally about an axis along which the first and second bodies are connectable. The step of removably connecting may include permitting relative movement translationally along and rotationally about an axis along which the first and second bodies are connectable.

The step of removably connecting may include inserting a protrusion of the second body into a recess defined by the first body. The step of removably connecting may include threading a threaded portion defined by an external surface of the protrusion into engagement with a threaded portion defined by an internal surface of the recess, and further threading the threaded portion of the protrusion until the entire threaded portion of the protrusion is located within the recess past the threaded portion of the recess. The method may further include the step of fixedly connecting the first body to the second body together by securing the assembly to the first implant component to prevent relative movement between the first and second bodies, including preventing rotation of the first body with respect to the second body by engaging an anti-rotation portion at a base end of the protrusion that has a non-circular cross section with an anti-rotation portion at a terminal end of the recess that has a non-circular cross section.

The method may further include the step of selecting a permanent implant component having the same dimensions as the assembly. The method may further include the steps of selecting the first body from a kit including a plurality of the first bodies each having a different size or shape, and selecting the second body from the kit including a plurality of the second bodies each having a different size or shape.

A third aspect of the present invention is an assembly for attachment to a first implant component, the assembly having a size and shape of a second implant component to be implanted together with the first implant component, including a first body defining a recess, the recess having an internal surface defining an annular groove, a second body including a protrusion insertable into the recess, the protrusion having an external surface defining an annular groove, and a split ring, wherein, when the split ring is disposed at least partially within the annular grooves of the protrusion and the recess, the first and second bodies are removably connected such that the first and second bodies are prevented from separating.

In accordance with other embodiments of the third aspect, the assembly may further include a locking screw configured to be secured through the first body and the second body and into a portion of the first implant component. The first and second bodies may be connectable along an axis and each may define lumens aligned with the axis in which the locking screw can be disposed. Tabs on one of the recess and the protrusion may be disposed within indents on the other of the recess and the protrusion to prevent relative rotation between the first and second bodies.

When assembled together, the first and second bodies may correspond to a cone body of a femoral hip assembly as the second implant component. The first body may define a femoral neck and an upper portion of a trunk of the cone body, and the second body may define a lower portion of the trunk of the cone body. The upper and lower portions of the trunk of the cone body may be connectable along a first axis, and the femoral neck of the first body may extend along a second axis that is angled with respect to the first axis. The trunk may define a maximum outer diameter and a maximum height, and the femoral neck may have a conical proximal surface for connecting with a femoral head, the conical proximal surface defining a center point of the proximal neck, and wherein the first body may define an offset distance measured perpendicularly from the first axis to the center point.

A modular femoral trialing kit may include a plurality of the first bodies according to the above, each having a different size or shape, and a plurality of the second bodies according to the above, each having a different size or shape. The maximum outer diameter of the trunk may be provided in sizes of 17, 19, 21, 23, 25, 27, 29, and 31 mm, or in other sizes. The maximum height of the trunk may be provided in sizes of 50, 60, 70, 80, 90, and 100 mm, or in other sizes. The offset distance of the femoral neck may be provided in sizes of 30, 34, 38, 40, and 44 mm, or in other sizes. The kit may further include a locking screw for securing the first body to the second body on a portion of an implant.

A fourth aspect of the present invention is a method of assembling an assembly for attachment to a first implant component, the assembly having a size and shape of a second implant component to be implanted together with the first implant component, including the steps of removably connecting a protrusion of a second body of the assembly into a recess defined by a first body of the assembly to move a split ring at least partially into an annular groove defined in an external surface of the protrusion and at least partially into an annular groove defined in an internal surface of the recess, such that the first and second bodies are prevented from separating, and positioning the assembly on the first implant component.

In accordance with other embodiments of the fourth aspect, the method may further include the step of fixedly connecting the first body to the second body together by securing a locking screw through the first body and the second body and into a portion of the first implant component. The method may further include the steps of assessing the biomechanics of a joint with the implanted assembly. The step of removably connecting may further include inserting tabs on one of the recess and the protrusion within indents on the other of the recess and the protrusion to prevent relative rotation between the first and second bodies. The method may further include the step of selecting a permanent implant component having the same dimensions as the assembly. The method may further include the steps of selecting the first body from a kit including a plurality of the first bodies each having a different size or shape, and selecting the second body from the kit including a plurality of the second bodies each having a different size or shape.

A fifth aspect of the present invention is an assembly for attachment to a first implant component, the assembly having a size and shape of a second implant component to be implanted together with the first implant component, including a first body defining a protrusion, and a second body including a recess into which the protrusion is insertable, wherein, when the protrusion is seated within the recess, the first and second bodies are removably connected such that the first and second bodies are prevented from separating.

In accordance with other embodiments of the fifth aspect, the assembly may further include a locking screw configured to be secured through the first body and the second body and into a portion of the first implant component. The first and second bodies may be connectable along a first axis and each may define lumens aligned with a second axis in which the locking screw can be disposed, the second axis being substantially perpendicular to the first axis. The protrusion may include a spring arm that presses against an internal wall of the recess when the protrusion is seated within the recess to prevent the first and second bodies from separating. The spring arm may include a convexly curved surface and the internal wall may be a concavely curved surface. The protrusion may include two spring arms that press against opposing internal walls, respectively, of the recess when the protrusion is seated within the recess to prevent the first and second bodies from separating. The two spring arms may include opposing convexly curved surfaces and the opposing internal walls may be opposing concavely curved surfaces. The protrusion may include a ledge configured to slide along the second axis into a groove of the recess, the groove having upper and lower surfaces to prevent movement of the ledge with respect to the groove along the first axis.

When assembled together, the first and second bodies may correspond to a cone body of a femoral hip assembly as the second implant component. The first body may define a femoral neck and an upper portion of a trunk of the cone body, and the second body may define a lower portion of the trunk of the cone body. The upper and lower portions of the trunk of the cone body may be connectable along a first axis, and the femoral neck of the first body may extend along a second axis that is angled with respect to the first axis. The trunk may defines a maximum outer diameter and a maximum height, and the femoral neck may have a conical proximal surface for connecting with a femoral head, the conical proximal surface defining a center point of the proximal neck, and wherein the first body may define an offset distance measured perpendicularly from the axis to the center point.

A modular femoral trialing kit may include a plurality of the first bodies according to the above, each having a different size or shape, and a plurality of the second bodies according to the above, each having a different size or shape. The maximum outer diameter of the trunk may be provided in sizes of 17, 19, 21, 23, 25, 27, 29, and 31 mm, or in other sizes. The maximum height of the trunk may be provided in sizes of 50, 60, 70, 80, 90, and 100 mm, or in other sizes. The offset distance of the femoral neck may be provided in sizes of 30, 34, 36, 38, 40, and 44 mm, or in other sizes. The kit may further include a locking screw for securing the first body to the second body on a portion of an implant.

A sixth aspect of the present invention is a method of assembling an assembly for attachment to a first implant component, the assembly having a size and shape of a second implant component to be implanted together with the first implant component, including the steps of removably connecting a protrusion of a first body of the assembly into a recess defined by a second body of the assembly, such that the first and second bodies are prevented from separating, and positioning the assembly on the first implant component.

In accordance with other embodiments of the sixth aspect, the method may further include the step of fixedly connecting the first body to the second body together by securing a locking screw through the first body and the second body and into a portion of the first implant component. The step of removably connecting may include moving the protrusion along a first axis and into the recess, and wherein the step of fixedly connecting may include inserting the locking screw through lumens of the first and second bodies that are aligned with a second axis that is substantially perpendicular to the first axis. The step of removably connecting may include moving a spring arm of the protrusion into contact with an internal wall of the recess so that the spring arm presses against the internal wall. The step of removably connecting may include moving two spring arms of the protrusion into contact with opposing internal walls, respectively, of the recess so that the spring arms presses against the respective internal walls.

The method may further include the steps of assessing the biomechanics of a joint with the implanted assembly. The method may further include the step of selecting a permanent implant component having the same dimensions as the assembly. The method may further include the steps of selecting the first body from a kit including a plurality of the first bodies each having a different size or shape, and selecting the second body from the kit including a plurality of the second bodies each having a different size or shape.

A seventh aspect of the present invention is an assembly for attachment to a first implant component, the assembly having a size and shape of a second implant component to be implanted together with the first implant component, including a first body including a plug having a projection, and a second body including a recess having an internal surface, the internal surface defining at least one indentation, wherein in a temporary configuration, when the plug is disposed within the recess and the projection is disposed at least partially within one of the at least one indentations, the first and second bodies are removably connected such that the first and second bodies are prevented from separating.

In accordance with other embodiments of the seventh aspect, the first and second bodies may be connectable along an axis and the at least one indentation may include two or more indentations, and wherein the first and second bodies may permit translational relative movement therebetween along the axis to locate the projection at least partially within different indentations of the two or more indentations without disconnecting the first body from the second body. In a fixed configuration, the first and second bodies may be prevented from separating while relative movement is not permitted between the first and second bodies. The assembly may further include a locking screw, wherein in the fixed configuration, the locking screw is secured through the first body and the second body and into a portion of the first implant component. The plug of the first body and the recess of the second body may be connectable along the axis and may each define lumens aligned with the axis in which the locking screw can be disposed. The plug may include a lever arm on which the projection is disposed. The locking screw may include a cylindrical head, and wherein, when the first and second bodies are in the fixed configuration, the cylindrical head may prevent the lever arm from moving and maintains the projection within one of the at least one indentations. The locking screw may include a head having a noncircular outer circumference defining a circular portion and a relief, and wherein the head may be placed in a first rotational orientation in which the circular portion is adjacent the lever arm and prevents the lever arm from moving and maintains the projection within one of the at least one indentations, and also in a second rotational orientation in which the relief is adjacent the lever arm and allows the lever arm to move. When the head of the locking screw is in the second rotational orientation, the first body may be moved along the axis with respect to the second body. A kit may include the assembly according to the above, and a tool having a prong, wherein the tool can be used to rotate the locking screw with the prong disposed adjacent to the relief.

Each indentation of the at least one indentation may be an annular groove. An external surface of the second body may include an indentation aligned with each of the at least one indentations. The first body may includes a second projection, and wherein in the temporary configuration, both of the projections may be disposed at least partially within one of the at least one annular grooves. The two or more indentations may be evenly spaced along the axis. When assembled together, the first and second bodies may correspond to a cone body of a femoral hip assembly as the second implant component. The first body may define a femoral neck of the cone body, and the second body may define a trunk of the cone body. The first and second bodies may be connectable along a first axis, and the femoral neck of the first body may extend along a second axis that is angled with respect to the first axis. The trunk may defines a maximum outer diameter, and the femoral neck may have a conical proximal surface for connecting with a femoral head, the conical proximal surface defining a center point of the proximal neck, and wherein the first body may define an offset distance measured perpendicularly from the first axis to the center point.

A modular femoral trialing kit may include a plurality of the first bodies according to the above, each having a different size or shape, and a plurality of the second bodies according to the above, each having a different size or shape. The maximum outer diameter of the trunk may be provided in sizes of 17, 19, 21, 23, 25, 27, 29, and 31 mm, or in other sizes. The offset distance of the femoral neck may be provided in sizes of 30, 34, 36, 38, 40, and 44 mm, or in other sizes. The kit may further include a locking screw for securing the first body to the second body on a portion of an implant.

A eighth aspect of the present invention is a method of assembling an assembly for attachment to a first implant component, the assembly having a size and shape of a second implant component to be implanted together with the first implant component, including the steps of removably connecting a plug of a first body of the assembly into a recess of a second body of the assembly by locating a projection of the plug within an indentation defined in an internal surface of the recess, such that the first and second bodies are prevented from separating, and positioning the assembly on the first implant component.

In accordance with other embodiments of the eighth aspect, the method may further include the step of locating the projection of the plug in another indentation defined in the internal surface of the recess without disconnecting the first body from the second body. The method may further include the step of fixedly connecting the first body to the second body together by securing the assembly to the first implant component to prevent relative movement between the first and second bodies. The step of fixedly connecting may include securing a locking screw through the first body and the second body and into a portion of the first implant component. The locking screw may include a cylindrical head and the plug may include a lever arm on which the projection is disposed, and wherein the step of fixedly connecting may include positioning the cylindrical head to prevent the lever arm from moving to maintain the projection within one of the at least one indentations. The locking screw may include a head having a noncircular outer circumference defining a circular portion and a relief and the plug includes a lever arm on which the projection is disposed, and wherein the step of fixedly connecting may include positioning the circular portion of the head adjacent the lever arm to prevent the lever arm from moving and to maintain the projection within one of the at least one indentations. The method may further include the step of positioning the relief of the head adjacent the lever arm to allow the lever arm to move. The method may further include the step of moving the first body along an axis along which the first and second bodies are connected with respect to the second body when the relief of the head adjacent the lever arm to adjust a height of the first body above a bottom of the second body. The step of positioning the relief of the head adjacent the lever arm may include engaging a prong of a tool adjacent to the relief and rotating the tool to rotate the locking screw. The method may further include the step of assessing the biomechanics of a joint with the implanted assembly.

The step of removably connecting may include permitting relative movement translationally along an axis along which the first and second bodies are connectable. The method may further include the step of selecting a permanent implant component having the same dimensions as the assembly. The method may further include the steps of selecting the first body from a kit including a plurality of the first bodies each having a different size or shape, and selecting the second body from the kit including a plurality of the second bodies each having a different size or shape.

BRIEF DESCRIPTION OF THE DRAWINGS

FIG. 1 is a front perspective view of a monolithic trial implant of the prior art.

FIG. 2 is a front perspective view of a trial assembly in accordance with one embodiment of the present disclosure.

FIG. 3 is a front perspective view of a first body and two second bodies of the trial assembly in accordance with the first embodiment.

FIG. 31 is a chart showing a matrix of size, length, and offset for various cone bodies in accordance with the third embodiment.

DETAILED DESCRIPTION

Figure 4:
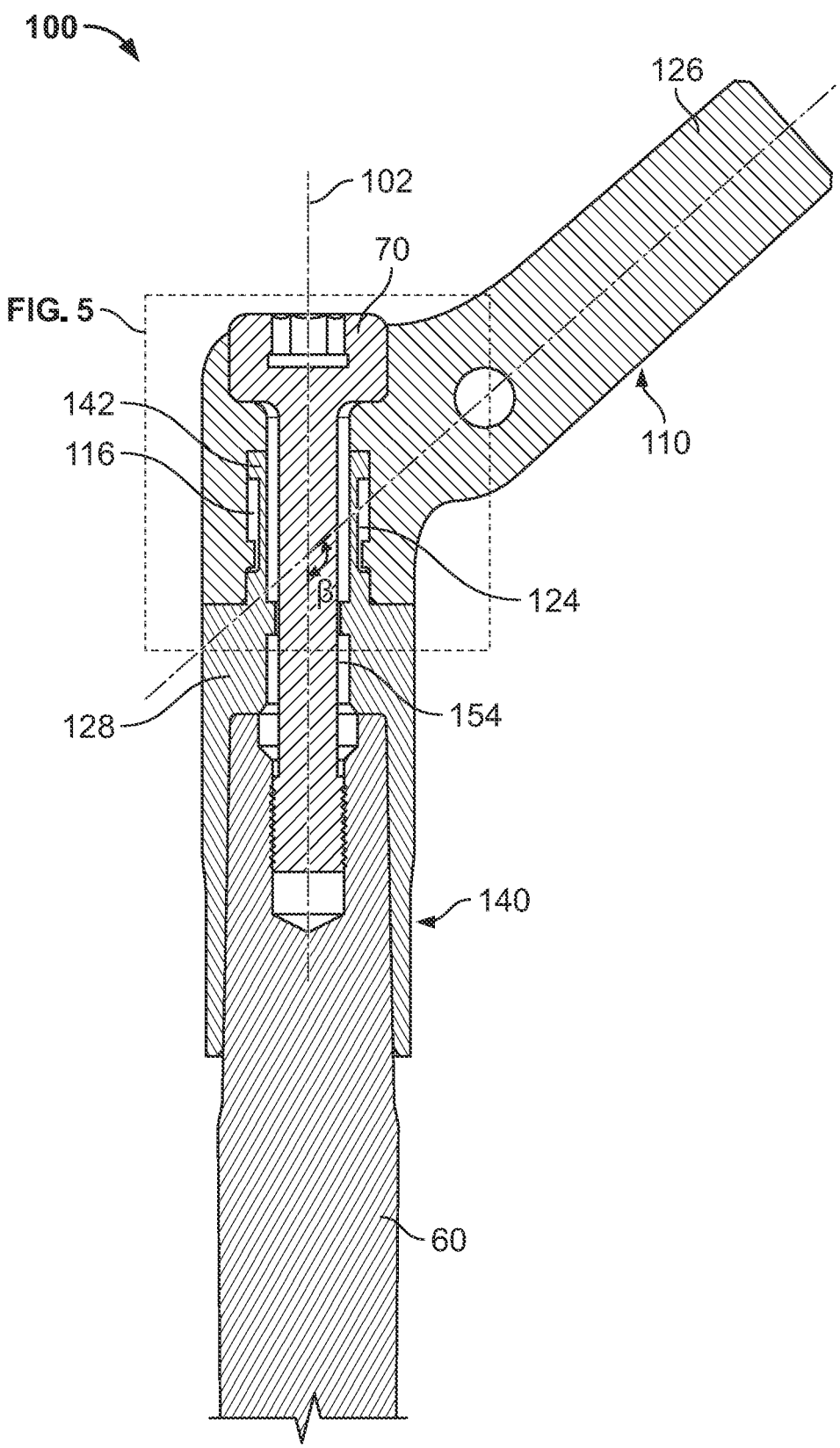
FIG. 4 is a front sectional view of the trial assembly shown in FIG. 2.
Figure 5:
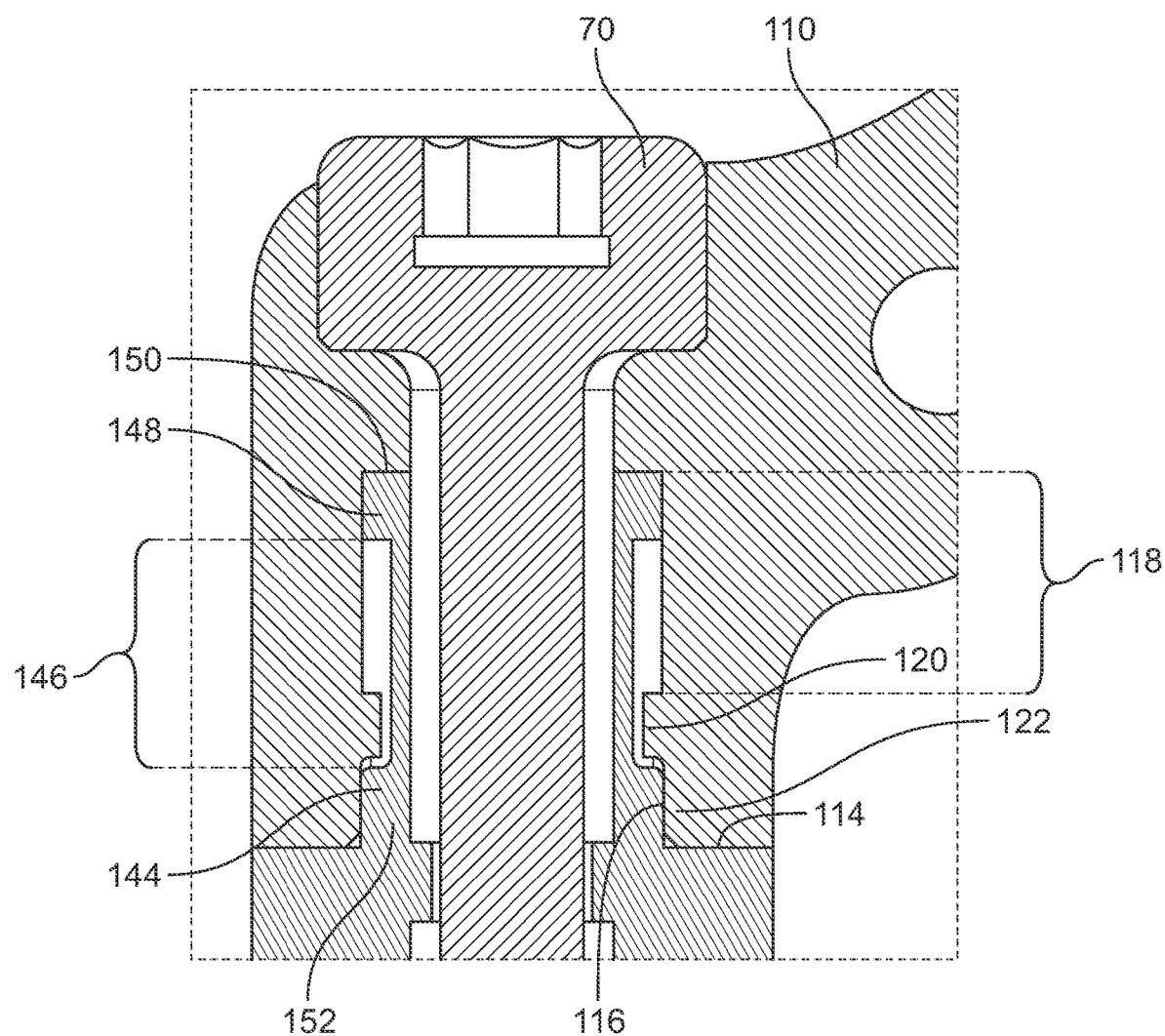
FIG. 5 is an enlarged front sectional view of a portion of the trial assembly shown in FIG. 4.
Figure 6:
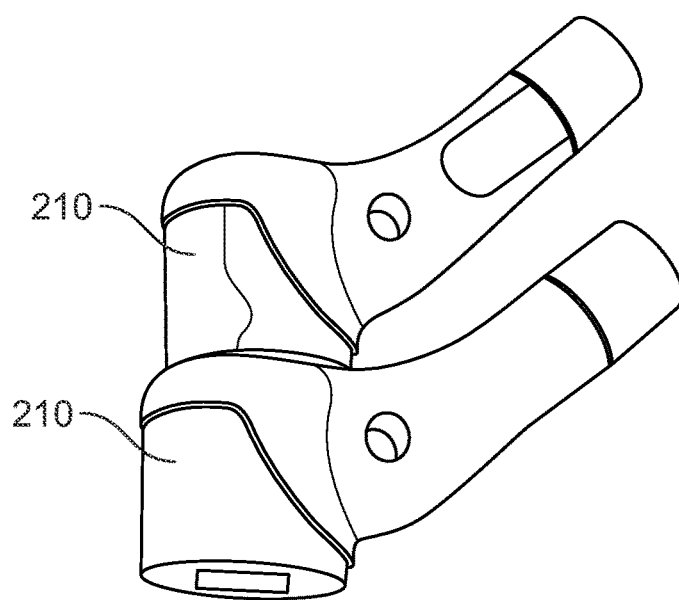
FIG. 6 is a front perspective view of two first bodies of a trial assembly in accordance with a second embodiment of the present disclosure.
Figure 7:
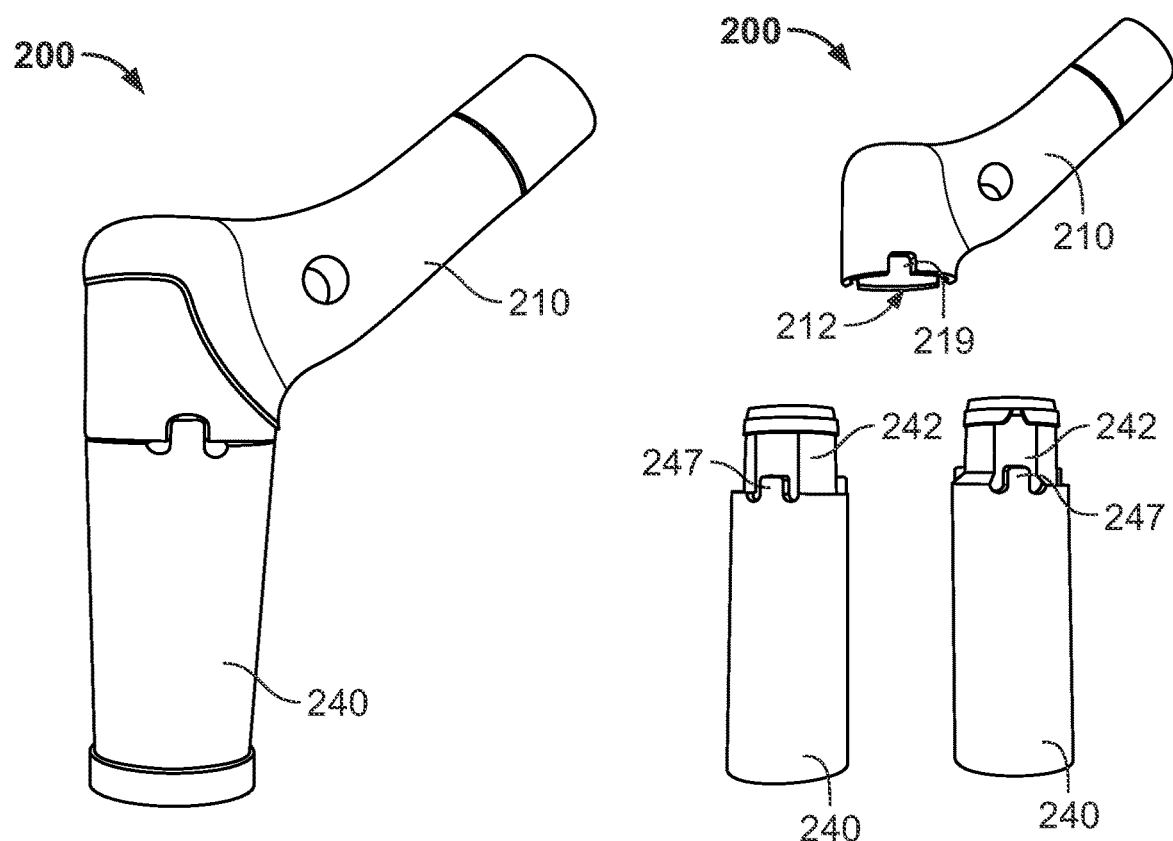
FIG. 7 is a front perspective view of the trial assembly in accordance with the second embodiment.
Figure 8:
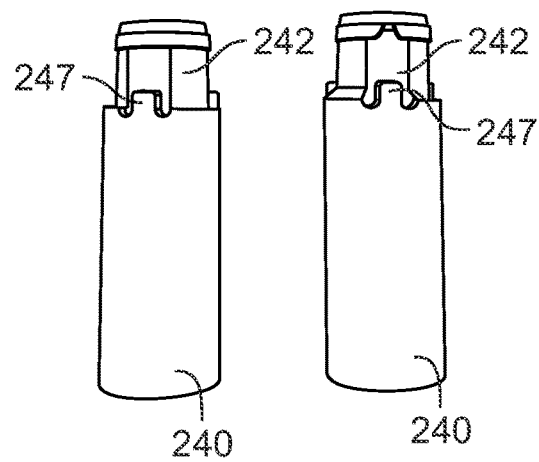
FIG. 8 is a front perspective view of a first body and two second bodies of the trial assembly in accordance with the second embodiment.
Figure 9:
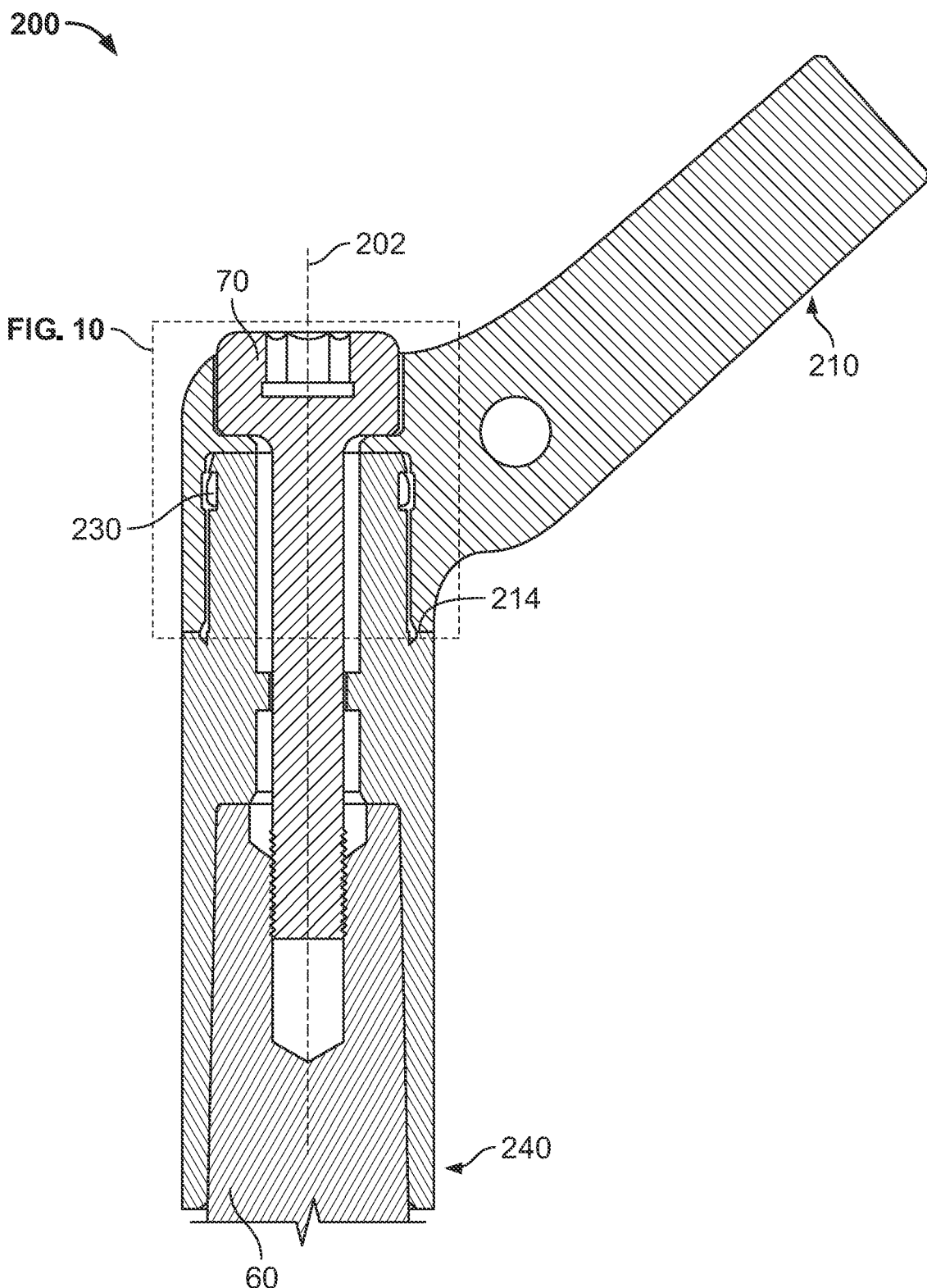
FIG. 9 is a front sectional view of the trial assembly shown in FIG. 7.
Figure 10:
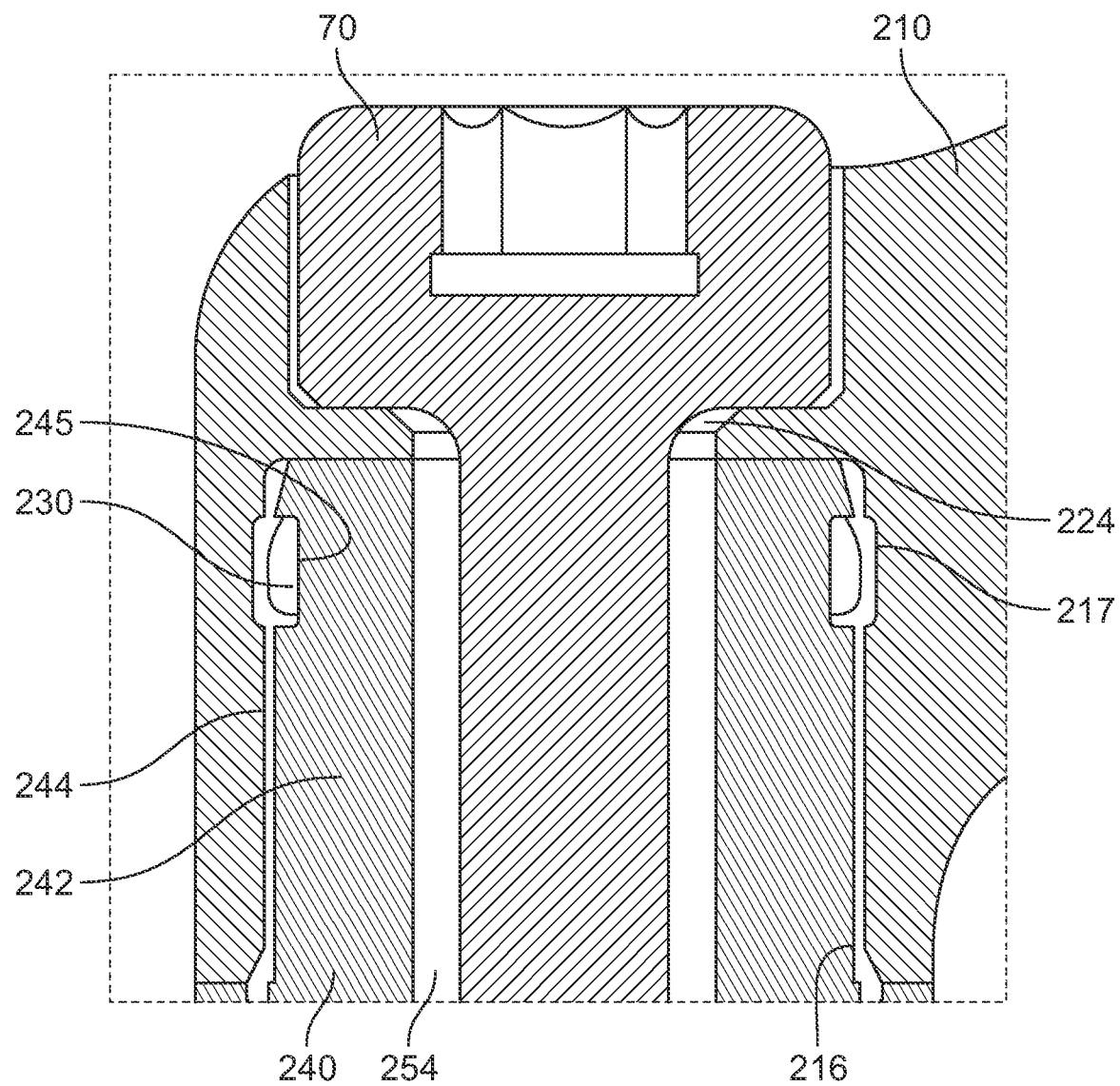
FIG. 10 is an enlarged front sectional view of a portion of the trial assembly shown in FIG. 9.

As shown in FIGS. 2-5, a first embodiment in accordance with the present invention is an assembly 100 used for trialing in the proximal femur. Assembly 100 includes a first body 110 and a second body 140 that are connectable in a temporary configuration and also in a fixed configuration, and a locking screw 70. Bodies 110, 140 are connectable along a vertical axis 102 shown in FIG. 4. When assembled, first and second bodies 110, 140 correspond to and have a size and shape of a cone body of a femoral hip assembly that can be attached to an implant component, such as a distal femoral stem 60.

First body 110 includes a recess 112 extending up from its bottom end to define a cavity. Recess 112 includes a terminal end 114 at the bottom end of first body 110 and an internal surface 116. Internal surface 116 defines a first non-threaded portion 118 and a second threaded portion 120, the latter of which is near the bottom end of first body 110 such that it is located closer to terminal end 114 of recess 112. Non-threaded portion 118 is disposed further into recess 112 and away from terminal end 114. At a portion adjacent terminal end 114, recess 112 has a non-circular, e.g. square, cross section that cooperates with a similar feature of second body 140 to function as an anti-rotation portion 122. That is, a portion of internal surface 116 extending upward from the bottom end of first body 110 is defined by the non-circular cross section. In other embodiments, the non-circular cross section can take on other shapes, such as triangular, oval, hexagonal, etc.

Opposite terminal end 114 of recess 112, a central portion of recess 112 continues upward to define a lumen 124 extending completely through to a top surface of first body 110. The upper end of lumen 124 defines a wider cavity, such that locking screw 70 can be disposed through lumen 124 with the head of locking screw 70 disposed in the wider cavity at its upper end.

The cone body with which assembly 100 corresponds generally includes a femoral neck and a trunk, with first body 110 corresponding to the femoral neck 126 and an upper portion of the trunk 128, and second body 140 comprising a lower portion of the trunk 128. Femoral neck 126 of first body 110 extends along an axis 104 that forms an angle β with respect to axis 102, as shown in FIG. 4.

Second body 140 includes a protrusion 142 that is insertable into recess 112 of first body 110. Protrusion 142 has an external surface 144 that defines a first non-threaded portion 146 and a second threaded portion 148, which is disposed adjacent a terminal end 150 of protrusion 142 and closer to terminal end 150 than non-threaded portion 146. Opposite terminal end 150 is a base end that has a non-circular, e.g. square, cross section to operate as an anti-rotation portion 152 when mated with anti-rotation portion 122 of first body 110. A lumen 154 extends through second body 140 along axis 102 and opens into a wider cavity at its lower end to accept a distal stem 60.

First and second bodies 110, 140 can be assembled in a temporarily connected configuration in which first and second bodies 110, 140 are prevented from separating, although relative movement is permitted between bodies 110, 140. This is facilitated by the threaded and non-threaded portions 118, 120, 146, 148 of bodies 110, 140 and their orientation and cooperation when bodies 110, 140 are assembled. During assembly, threaded portions 120, 148 of recess 110 and protrusion 140, respectively, engage one another as protrusion 140 is screwed into recess 110. Then, threaded portions 120, 148 disengage from one another such the entire threaded portion 148 of protrusion 140 is located within recess 112 past threaded portion 120.

The heights of the threaded and non-threaded portions 118, 120, 146, 148 along axis 102, as well as the heights of anti-rotation portions 122, 152, allow for first body 110 to move translationally along axis 102 and rotationally about axis 102 with respect to second body 140. That is, protrusion 142 can move up and down translationally along axis between a position where its terminal end 150 contacts the upper end of recess 112 and a position where threaded portions 120 and 148 contact one another. Because there is no threaded connection in this position, protrusion 142 can also move rotationally about axis 102 with respect to recess 112. In this temporarily connected configuration, first and second bodies 110, 140 cannot separate on their own due to the juxtaposition of threaded portions 120, 148. Only when threaded portions 120, 148 are reengaged and threaded past one another can first and second bodies 110, 140 be separated.

From the temporarily connected configuration, assembly can be placed into its fixedly connected configuration upon the insertion of locking screw 70 through lumen 124 of first body 110, lumen 154 of lower body 140, and into a distal stem 60 where it is secured by being threaded into the stem 60. This secures first and second bodies 110, 140 together and against the distal stem 60 from any further relative movement between one another. Locking screw 70 prevents relative translational movement of bodies 110, 140 along axis 102 whereas anti-rotation portions 122, 152 prevent relative rotational movement of bodies 110, 140 about axis 102.

A modular kit for a trialing procedure includes a plurality of first bodies 110 each having a different size or shape and a plurality of second bodies 140 each having a different size or shape. Each one of first bodies 110 is connectable with one or more of second bodies 140 to form different, uniquely configured assembly 100. The variation of first and second bodies 110, 140 allows the assemblies 110 to have different maximum diameters of the trunk 128, different maximum heights of the trunk 128, and different offset distances of the femoral neck 126. Incremental sizes of maximum diameters of the trunk 128 can be 17, 19, 21, 23, 25, 27, 29, and 31 mm, among other sizes. Any other sizes within or outside this range can be used. In some embodiments of the kit, a first body 110 having a specifically sized maximum diameter of the trunk 128 can only be connected with a second body 140 having an identically sized maximum diameter of its trunk 128, though other parameters of the bodies 110, 140 may be different. Incremental sizes of maximum heights of the trunk 128 can be 50, 60, 70, 80, 90, and 100 mm, among other sizes. Any other sizes within or outside this range can be used. Incremental sizes of offset distances of the femoral neck 126 of first body 110 can be 30, 34, 36, 38, 40, and 44 mm, among other sizes. Any other sizes within or outside this range can be used. Thus, the modularity of assembly 100 allows surgeons to build assemblies having a particular diameter, height, and offset for a given application while requiring fewer components to resemble all versions of the permanent implant. That is, the modularity of the system requires fewer components than a traditional trialing system in which one trial is required for each permanent implant. In some embodiments of the kit, a pair of bodies 110, 140 sharing a maximum diameter can be offered in multiple heights, and each of these combinations can be offered in multiple offset distances.

While assembly 100 is configured for use in the proximal femur, other two-piece trial implants are contemplated for use in other joints, such as the hip, knee, shoulder, and elbow, among others. The connectable two-piece trial can be used in any scenario in which multiple aspects of the implant can be varied in size and/or shape so that a combined two-piece trial would allow for a reduction in the number of components needed in the operating room for a trialing procedure. In addition, it is also contemplated that the two-piece construct can be utilized as a final implant in any of these anatomical locations when it can be properly secured and stabilized for long-term fixation.

A method of assembling assembly 100 for attachment to a first implant component, such as a distal femoral stem 60, includes a user first selecting an initial size of first and second bodies 110, 140 based on the results of bone preparation. The user then removably connects first body 110 to second body 140 in the temporarily connected configuration, such that first and second bodies 110, 140 are prevented from separating while permitting relative movement therebetween. This is facilitated by inserting protrusion 142 into recess 112, which involves threading threaded portion 148 of protrusion 142 into engagement with threaded portion 120 of recess 112 until the entire threaded portion 148 of protrusion 142 is located within recess 112 past the threaded portion 120 of recess 112.

The method can be performed in the operating room, where a user selects the first and second bodies 110, 140 each from a kit including a plurality of first bodies 110 of different sizes and/or shapes and a plurality of second bodies 140 of different sizes and/or shapes. With the benefit of a kit of various assembly components, this permits the user to build an assembly 100 that meets the size and shape specifications for a particular surgery. Since assembly 100 is used for a trialing procedure, the components can be mated and put in place for trialing by the user with the foresight that it may indeed be necessary to disassemble the trial and substitute another one or both of first and second bodies 110, 140 to provide a trial assembly 100 that results in an acceptable fit for the patient.

When trialing with an assembly as provided herein, the combination of elements can require additional concentration by the user to maintain the configuration and alignment of the parts, i.e. bodies 110, 140, while the assembly is moved toward and assembled to an implant component or bone on the patient. Assembly 100 allows this task to be done with much greater reliability and less risk of disassembly given that bodies 110, 140 can be mated in the temporarily connected configuration. This can be done by the user at the time of selecting each body 110, 140, and then assembly 100 can be easily moved to the implantation site with assurance on behalf of the user that the assembly 100 will stay assembled during this process. The variability allowed in the translational and rotational movement of the bodies 110, 140 with respect to one another allows the user with the freedom to manipulate the final positioning and orientation of assembly 100 easily.

Once assembly 100 is assembled and moved to the implantation site, assembly 100 is then positioned on distal femoral stem 60. Next, first body 110 is fixedly connected to second body 140 in the fixedly connected configuration by securing assembly 100 to stem 60 to prevent relative movement between first and second bodies 110, 140. This is done by securing locking screw 70 through lumen 124 in first body 110 and through lumen 154 of second body 140 and into a portion of stem 60. The distal end of locking screw 70 is threaded into stem 60, while a head of the screw is recessed to be substantially flush with the top of first body 110. Anti-rotation portions 122 and 152 mate to prevent relative rotation between bodies 110, 140 in this assembled configuration.

With assembly fixedly connected to distal stem 60, the user can then perform a trialing procedure by installing a trial femoral head on femoral neck 126, reducing the femoral joint, and assessing the biomechanics of the joint with the implanted assembly 100. If the user determines that the fit of assembly 100 is not appropriate, assembly can be removed by unscrewing locking screw 70 and disassembling locking screw and assembly 100 from stem 60. Then one or both of first and second bodies 110, 140 can be replaced and a new, uniquely configured assembly 100 can be assembled and trialed per the method above. Once the proper fit is achieved, the user can select and install a permanent implant that corresponds to the dimensions of the properly fitted assembly 100.

The benefits of the construction and use of assembly 100 and its modularity are a reduced SKU count, a reduced tray size for trialing, and a trial implant that it is easy to assemble and disassemble and is cheaper to manufacture than conventional one-to-one trial systems.

FIGS. 6-10 depict a second embodiment in accordance with the present invention, which is an assembly 200 also used for trialing in the proximal femur and connected via a different mechanism. Several aspects of assembly 200 are similar to those of assembly 100, and like numerals are used to reference like components.

Assembly 200 includes locking screw 70 along with a first body 210 and a second body 240 that are connectable in a temporary configuration and in a fixed configuration in a similar manner to assembly 100. First body 210 has a recess 212 extending up from its bottom end to define a cavity. Recess 212 includes an internal surface 216 that defines an annular groove 217 therein. Recess 212 extends upward into a lumen 224 to facilitate passage of locking screw 70. Second body 240 includes a protrusion 242 insertable into recess 212 and having an external surface 244 defining an annular groove 245 therein. A lumen 254 extends through second body 240 along axis 202 and accepts distal stem 60 at a cavity in its lower end. A split ring 230 is initially disposed in one of annular grooves 217 and 245. Split ring 230 is a C-shaped clip that allows for slight expansion and compression of its diameter so that it can be fitted within recess 212 and positioned over protrions 242.

First and second bodies 210, 240 can be assembled by inserting protrusion 242 into recess 212 until annular grooves 217 and 245 are aligned so that split ring 230 is disposed at least partially within both annular grooves 217, 245. This places first and second bodies 210, 240 in their temporarily connected configuration in which they are removably connected and prevented from separating. That is, when protrusion 242 is fit into recess 212 to the point where split ring 230 snaps into annular grooves 217 and 245, first and second bodies 210, 240 are retained together unless a force is provided that overcomes a force needed to flex split ring 230 out of one or both grooves 217, 245. This force is calibrated to be high enough to prevent accidental disengagement of first and second bodies 210, 240, while also allowing first and second bodies 210, 240 to be pulled part by a user using one or two hands.

At the base of protrusion 242 outside its external surface 244 are a series of tabs 247 spaced radially about the circumference of protrusion 242. Tabs 247 are configured to mate within indents 219 at a terminal end 214 of recess 212. This provides non-circular sections of each of protrusion 242 and recess 212 that can be mated to prevent relative rotation between first and second bodies 210, 240 when they are assembled in the temporarily connected configuration. In other embodiments, the tabs 247 and indents 219 can be switched so that they are located on the opposite ones of the protrusion 242 and recess 212.

Because of the way split ring 230 fits into grooves 217, 245 in one position along axis 202, and because this position coincides with tabs 247 being disposed within indents 219, the temporarily connected configuration of assembly 200 does not necessarily permit for first body 210 to move translationally along axis 202 and rotationally about axis 202 with respect to second body 240. Before split ring 230 is fully seated in both grooves 217, 245, relative rotation is permitted and relative translation is also permitted up to the point at which protrusion 242 is fully seated within recess 212. In other embodiments, groove 217 and/or groove 245 can be lengthened into recessed annular areas along axis 202 so that some translational movement is permitted once split ring 230 is seated within both grooves.

After assembly is placed in its temporarily connected configuration, assembly 200 can be placed into its fixedly connected configuration upon the insertion of locking screw 70 through lumen 224 of first body 210, lumen 254 of lower body 240, and into a distal stem 60 to secure first and second bodies 210, 240 from further relative movement.

Of course assembly 200 is provided in the same type of modular kit to provide the same benefits as assembly 100. Assembly 200 can also be provided for use in different bones and joints besides just the femur.

A method of assembling assembly 200 follows the same steps as that for assembly 100, though the assembly of sliding protrusion 242 into recess 212 includes moving split ring 230 at least partially into annular groove 245 of protrusion 242 and at least partially into annular groove 217 of recess 212. This includes aligning tabs 247 to be inserted into indents 219. As recess 212 slides over protrusion 242, split ring 230 retracts due to the internal diameter of recess 212. Once split ring 230 engages with the large internal diameter of recess 217, split ring 230 expands, thereby retaining the two pieces together. Other aspects of the assembly method are the same as those described above. The temporarily connected configuration similarly allows the user the ability to mate the bodies 210, 240 of the assembly 200 with assurance that they can be manipulated in a trialing procedure without disassembling.

A third embodiment in accordance with the present invention is shown in FIGS. 11-19. An assembly 300 used for trialing in the proximal femur uses a different means of connection. Several aspects of assembly 300 are similar to those of assemblies 100 and 200, and like numerals are used to reference like components. Assembly 300 includes locking screw 70 with a first body 310 and a second body 340 that are connectable in a temporary configuration and also in a fixed configuration.

Figure 11:
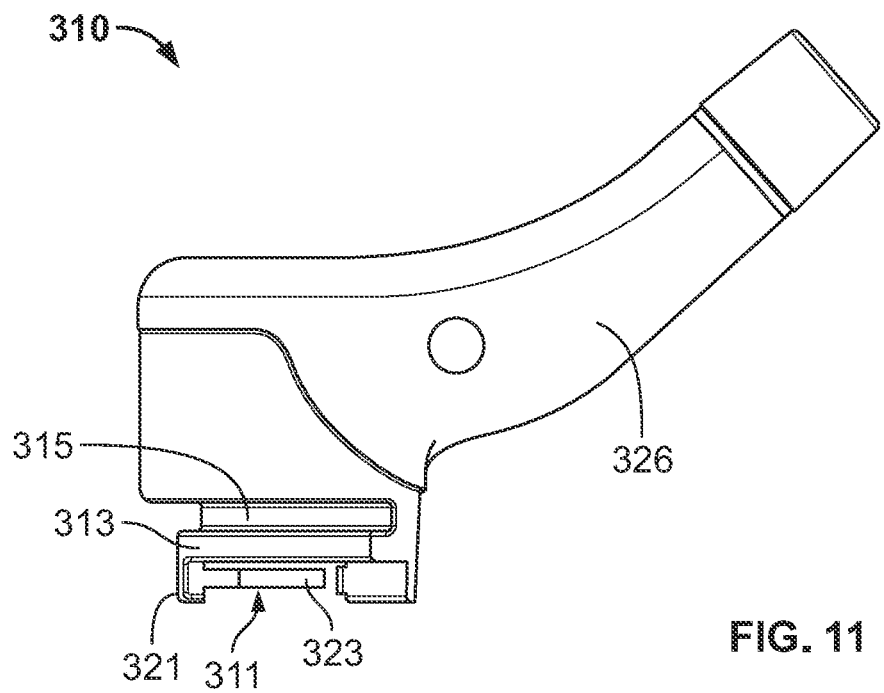
FIG. 11 is a front plan view of a first body of a trial assembly in accordance with a third embodiment of the present disclosure.
Figure 12:
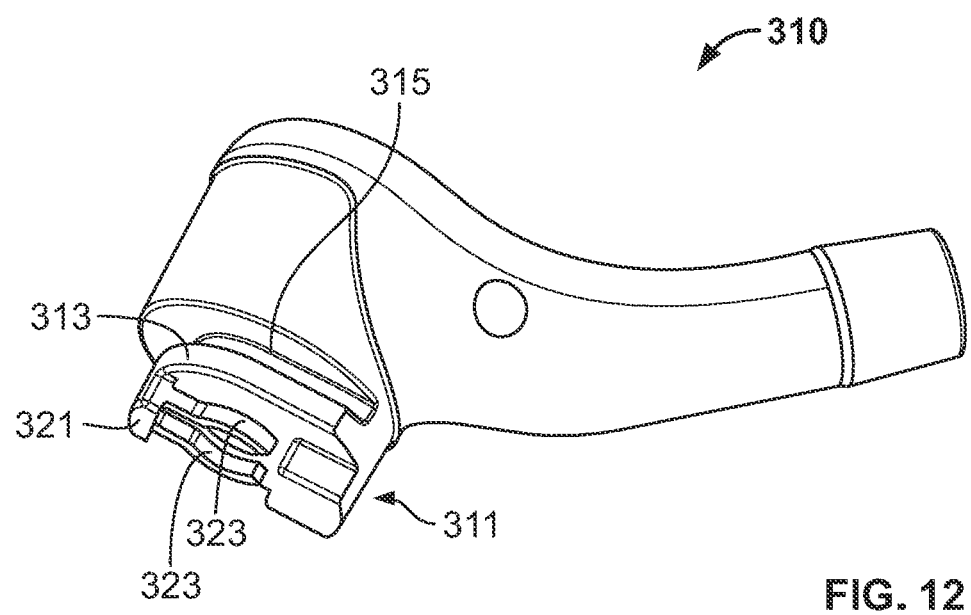
FIG. 12 is a front perspective view of the first body of the trial assembly in accordance with the second embodiment.
Figures 13, 14, 15:
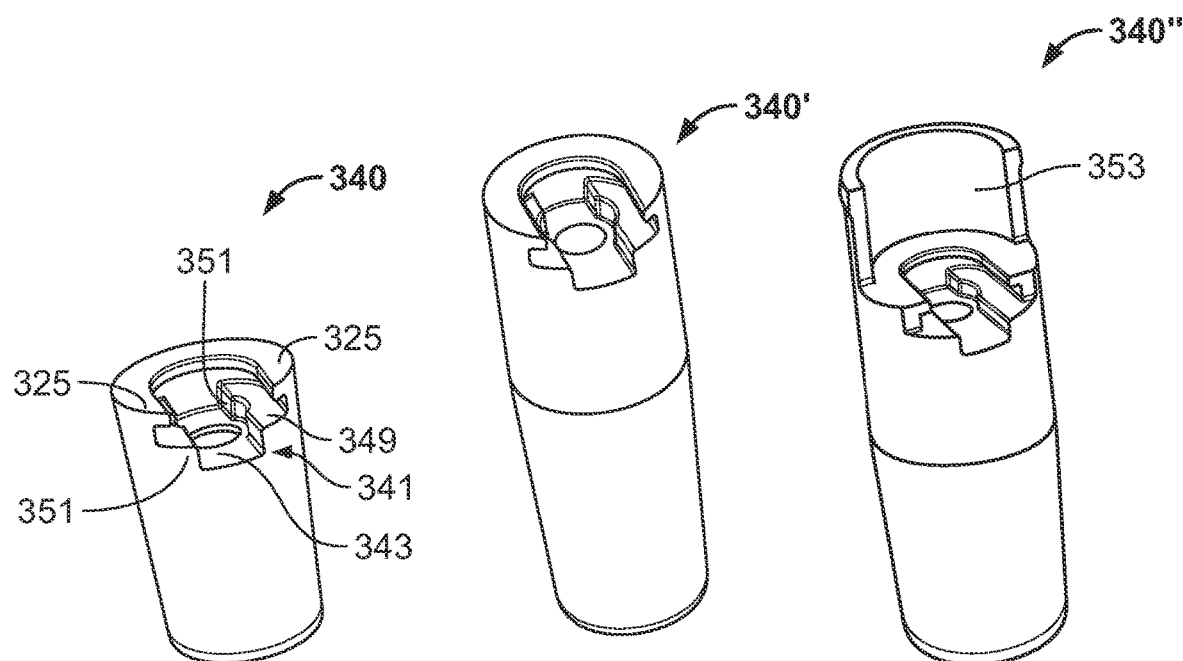
FIGS. 13-15 are front perspective views of second bodies of the trial assembly in accordance with the second embodiment.

As shown in FIGS. 11-13, first body 310 defines a protrusion 311 extending downward from its bottom end that is insertable into a recess 341 located at an upper end of second body 340. From the bottom end of first body 310 extending downward, protrusion 311 includes a neck or groove 315 and a horizontally extending rib or ledge 313 that is wider than neck 315 so that neck 315 creates a somewhat annular, horizontal channel located between rib 313 and the bottom end of first body 310. Rib 313 can slide along a horizontal axis 303 into neck 315 during assembly.

Beneath rib 313, a stop 321 extends downward and two spring arms 323 are anchored to stop 321 so that arms 323 each extend in a horizontal direction that is generally planar to rib 313. Spring arms 323 are contoured to each have a C-shape around a lumen 324 that extends completely through protrusion 311 to a top surface of first body 310. The upper end of lumen 324 defines a wider cavity for the head of locking screw 70. In other embodiments, projection 311 can have only spring arm or can have more than two spring arms.

As shown in FIG. 13, recess 341 extends down from the top end of second body 340 to define a cavity. Recess 341 includes a narrow channel 343 at its terminal end and a wider channel 349 above narrow channel 343. Narrow channel 343 houses stop 321 and spring arms 323 of protrusion 311 when first and second bodies 310, 340 are assembled together. More specifically, narrow channel 343 has two concave surfaces 351 that mate with the convex C-shaped contours of spring arms 323. When first body 310 is assembled to second body 340, protrusion 311 is slid horizontally into recess 341 until spring arms 323 snap into place to press against the internal wall of narrow channel 343 at concave surfaces 351. This snap fit allows second body 340 to be seated within first body 310 and prevents first and second bodies 310 and 340 from separating absent an opposing force applied to purposely separate the bodies.

Figures 16, 17, 18:
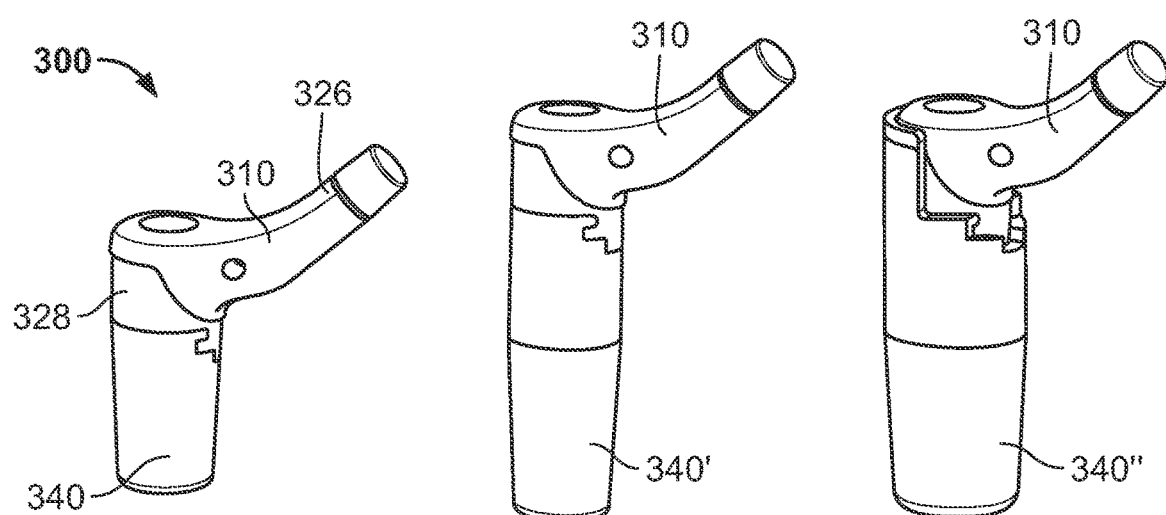
FIGS. 16-18 are front perspective views of trial assemblies including the respective second bodies of FIGS. 13-15 in accordance with the second embodiment.

When first and second bodies 310, 340 are assembled, as depicted in FIG. 16, wider channel 349 accommodates horizontal rib 313 and two ledges 325 extend above rib 313 to seat within neck 315 of first body 310. This further guides the fit between bodies 310, 340 and enhances their connection once assembled by preventing movement of rib 313 with respect to neck 315 along a vertical axis 302. Thus, once protrusion 311 is seated within recess 341, first and second bodies 310, 340 are removably connected such that they are prevented from separating.

FIG. 14 depicts a taller second body 340' that is otherwise similar in structure to second body 340. FIG. 15 depicts a second body 340" that is also taller than second body 340, but that includes a hood 353 extending upward from its upper surface that acts as a sort of back stop during assembly of first body 310. Second body 340' is shown attached to first body 310 in FIG. 17. Second body 340" is shown in FIG. 18 attached to first body 310, which mates with hood 353.

Figure 19:
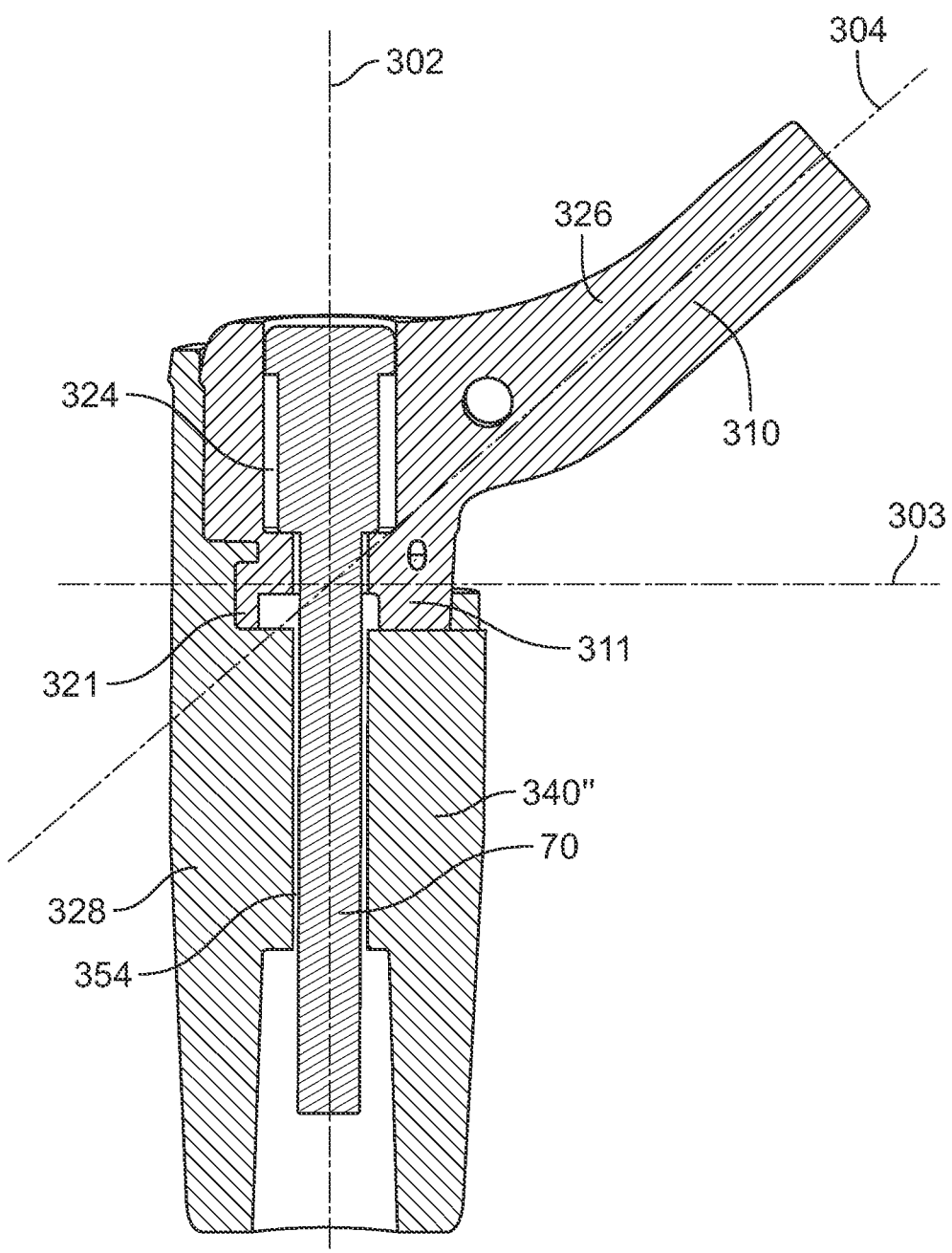
FIG. 19 is a front sectional view of the trial assembly shown in FIG. 18.
Figure 20:
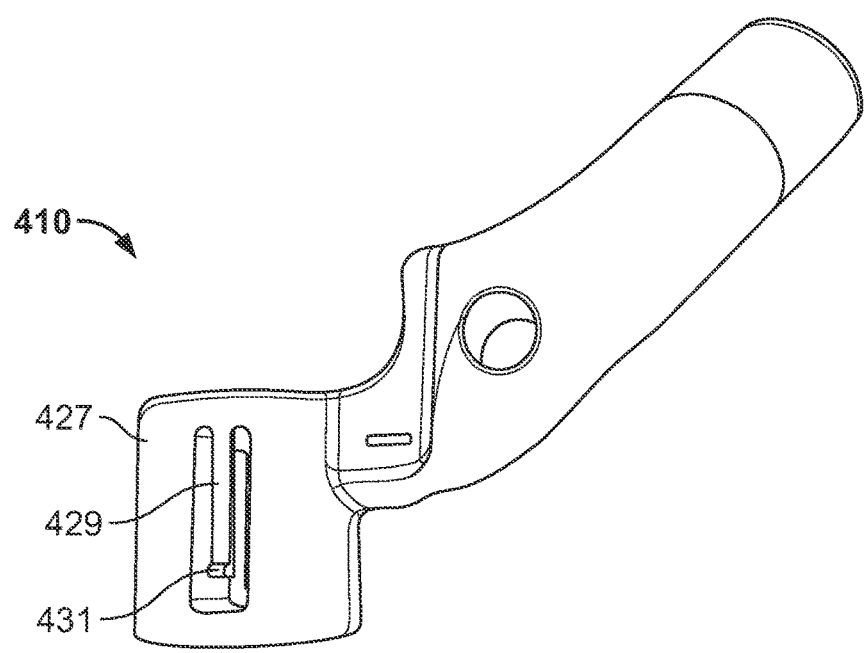
FIG. 20 is a front perspective view of a first body of a trial assembly in accordance with a fourth embodiment of the present disclosure.
Figure 21:
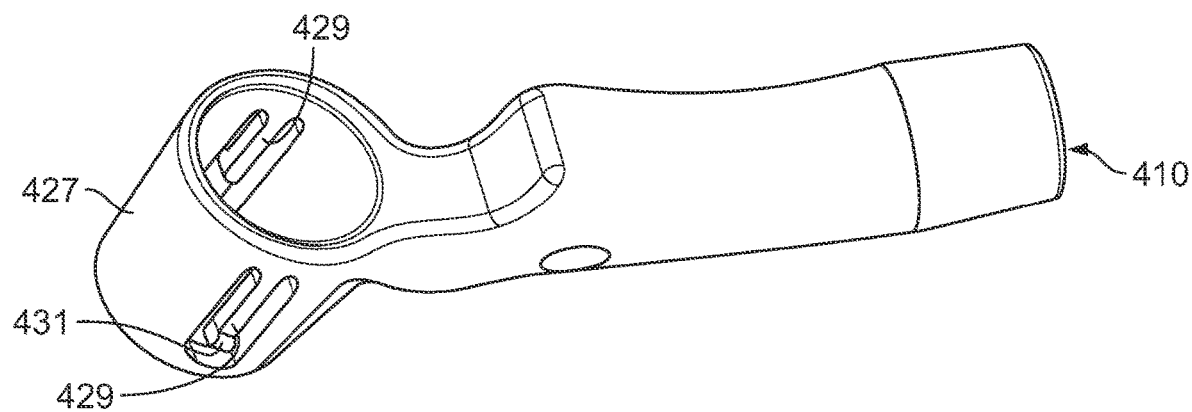
FIG. 21 is top perspective view of the first body shown in FIG. 20.

The cone body with which assembly 300 corresponds generally includes a femoral neck and a trunk, with first body 310 corresponding to a femoral neck 326 and an upper portion of the trunk 328, and second body 340 comprising a lower portion of the trunk 328. Femoral neck 326 extends along an axis 304 that forms an angle θ with respect to horizontal axis 303 along which bodies 310, 340 are connectable, as shown in FIG. 19. A lumen 354 extends through second body 340 along vertical axis 302 and opens into a wider cavity at its lower end to accept a distal stem 60.

First and second bodies 310, 340 can be assembled in a temporarily connected configuration in which first and second bodies 310, 340 are prevented from separating, when spring arms 323 of first body 310 press against the internal wall of narrow channel 343 at concave surfaces 351 of second body 340. From the temporarily connected configuration, assembly can be placed into its fixedly connected configuration upon the insertion of locking screw 70 through a lumen 324 of first body 310, lumen 354 of lower body 340, and into a distal stem 60 where it is secured by being threaded into the stem 60. This secures first and second bodies 310, 340 together and against the distal stem 60 from any further relative movement between one another. Assembly of first and second bodies 310, 340 occurs along horizontal axis 303, while locking screw 70 is disposed through lumens 324, 354 that are aligned with vertical axis 302. Axis 302 is substantially perpendicular to axis 303.

Of course, as described above, modular kits can be provided for trialing procedures including a plurality of differently sized first and second bodies of any of the embodiments described herein. Also, differently sized bodies of more than one of the embodiments described herein can be assembled into a kit. Assembly 300, as well as any embodiment described herein, can be modified geometrically to be used in other joints, such as the hip, knee, shoulder, and elbow, among others. FIG. 31 is a chart showing a matrix of size, length, and offset for various cone bodies in accordance with the third embodiment of assembly 300.

A method of assembling assembly 300 is similar to the methods described above except for the different connection of assembly 300. The method includes removably connecting protrusion 311 of first body 310 into recess 341 of second body 340 in the temporarily connected configuration, such that first and second bodies 310, 340 are prevented from separating. Assembly 300 allows this to be done with great reliability and low risk of disassembly given that bodies 310, 340 can be mated in the temporarily connected configuration. A locking screw 70 can then be secured through lumen 324 in first body 310 and through lumen 354 of second body 340 and into a portion of stem 60. The distal end of locking screw 70 is threaded into stem 60, while a head of the screw is recessed to be substantially flush with the top of first body 310. With assembly 300 fixedly connected to distal stem 60, the user can then perform a trialing procedure by installing a trial femoral head on femoral neck 326, reducing the femoral joint, and assessing the biomechanics of the joint with the implanted assembly 300. Further iterations of the method can be performed as necessary, as facilitated by the trialing kit.

Figure 22:
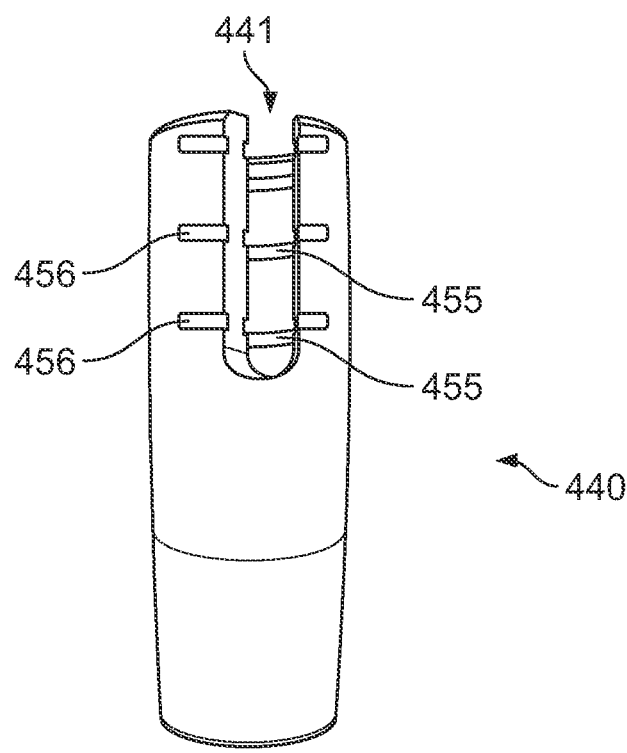
FIG. 22 is a front perspective view of a second body of the trial assembly in accordance with the fourth embodiment.
Figure 23:
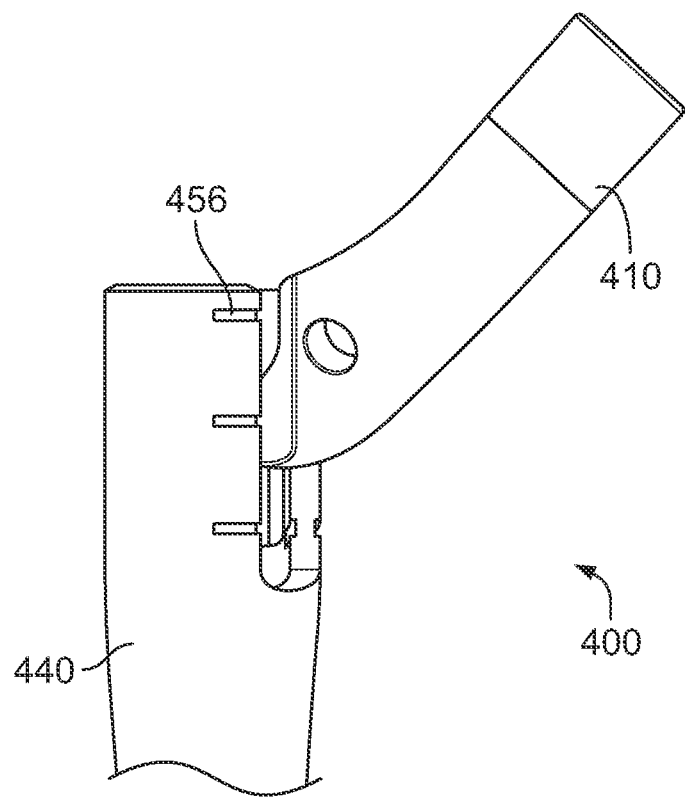
FIG. 23 is a front perspective view of the trial assembly in accordance with the fourth embodiment.
Figure 24:
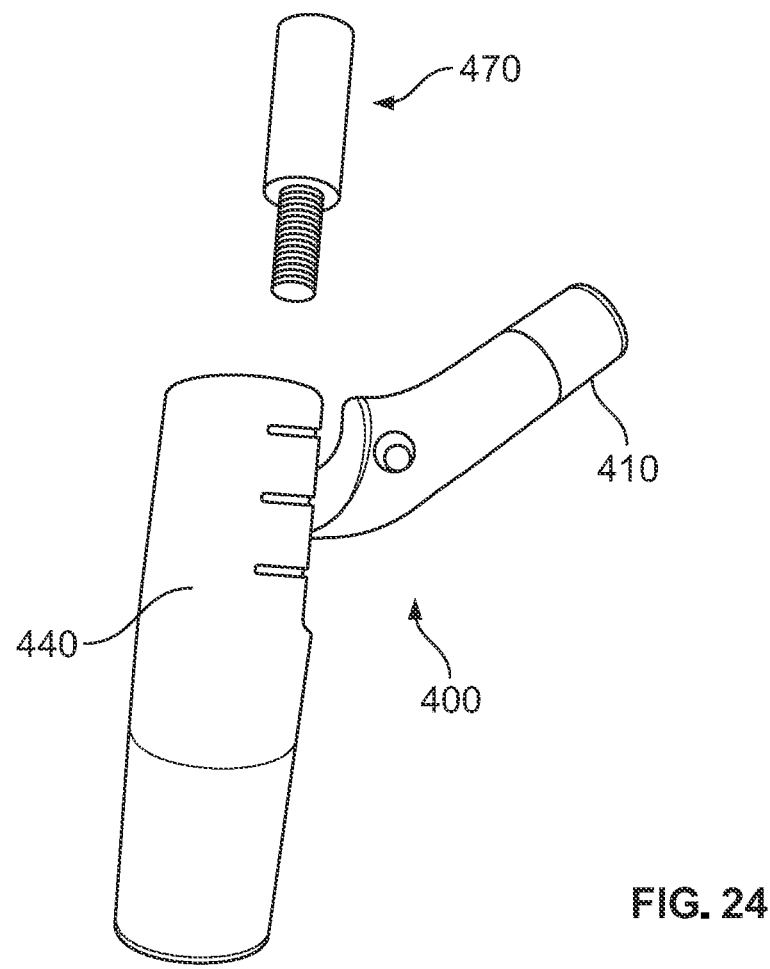
FIG. 24 is a front perspective view of the trial assembly in accordance with the fourth embodiment together with a locking screw.
Figure 25:
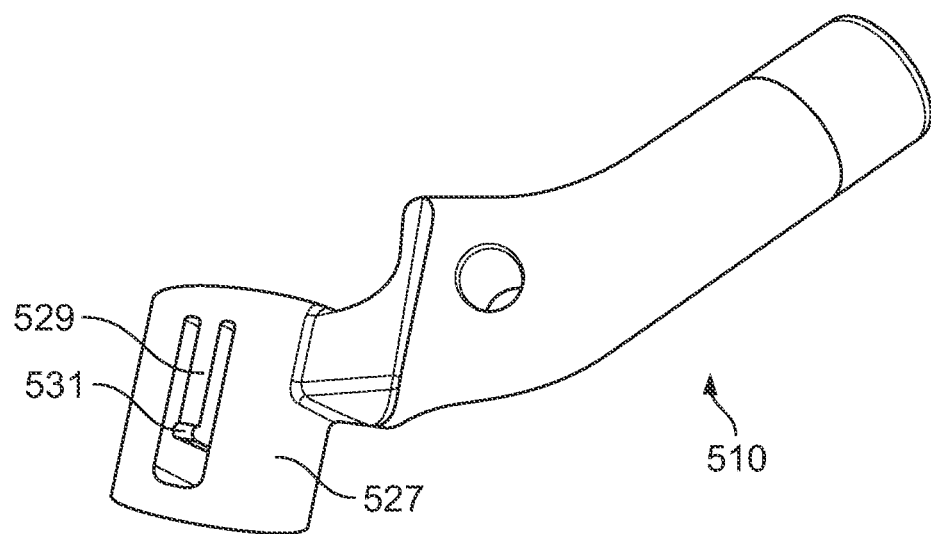
FIG. 25 is a front perspective view of a first body of a trial assembly in accordance with a fifth embodiment of the present disclosure.
Figure 26:
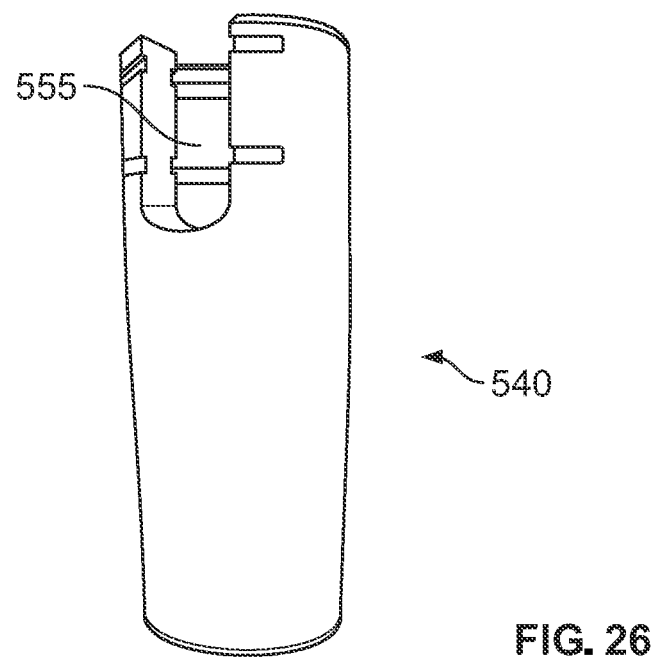
FIG. 26 is a front perspective view of a second body of the trial assembly in accordance with the fifth embodiment.
Figure 27:
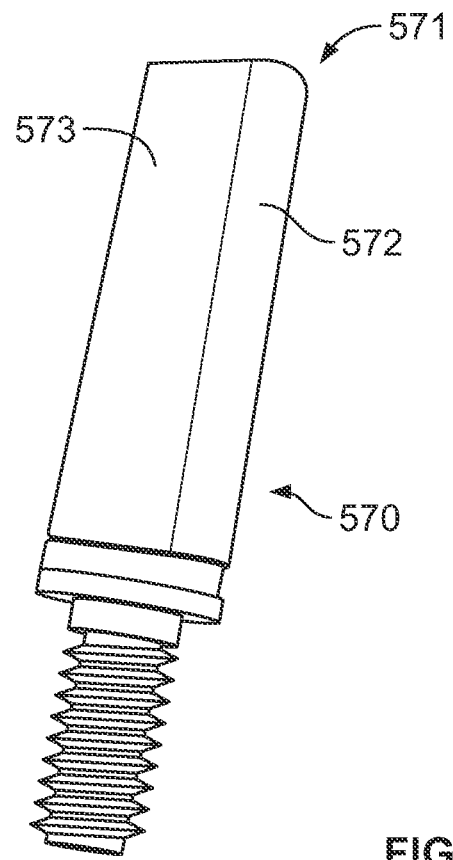
FIG. 27 is a front perspective view of a locking screw of the trial assembly in accordance with the fifth embodiment.

As shown in FIGS. 20-24, a fourth embodiment in accordance with the present invention is an assembly 400 used for trialing in the proximal femur. Assembly 400 is similar to those above, with like elements numbered similarly. Assembly 400 includes a first body 410 and a second body 440 that are connectable in a temporary configuration and also in a fixed configuration, and a locking screw 70. Bodies 410, 440 are connectable along a vertical axis as shown in FIG. 23.

First body 410 has a plug 427 that has on each opposite side a flexible tab or lever arm 429 with a projection or nub 431 at its free end. A lumen 424 extends completely through plug 427 so that lever arm 429 is free to flex in and out of lumen 424. While two lever arms 429 are provided in cutouts in the annular wall of plug 427, one or three or more lever arms 429 can be provided.

Second body 440 includes a recess 441 that forms an upper portion of a lumen within second body 440. Recess 441 has an internal cylindrical surface that defines three annular indentations or grooves 442. In other embodiments, at least one annular indentation is provided, and preferably two or more are provided and are preferably evenly spaced along a vertical axis of recess 441. To mark annular indentations 442 to the user, external markings or indentations 456 are provided on an external surface of second body 440, as shown in FIGS. 22 and 23.

First and second bodies 410, 440 can be assembled in a temporarily connected configuration in which plug 427 is disposed within recess 441 such that projections 431 are disposed at least partially within one of indentations 442. In this configuration, first and second bodies 410, 440 are removably connected and prevented from separating. The force provided by lever arm 429 on projection 431 is such that first and second bodies 410, 440 can be moved or translated relative to one another so that projections 431 can be located within different indentations 442 without disconnecting first body 410 from second body 440, i.e. without removing plug 427 from recess 441. This allows a user to set a particular height of first body 410 with respect to second body 440 during a trialing procedure, such that assembly 400 can be said to be of variable height.

Assembly 400 can be placed into its fixedly connected configuration by inserting a locking screw 470 lumen 424 of first body 410 and threading it into a distal stem through recess 441 of second body 440. Locking screw 470 has an elongated head such that the large diameter of the head extends along a majority of the length of locking screw 470, with a narrower threaded portion at its distal end. When locking screw 470 is disposed within lumen 424 of plug 427, enlarged diameter of locking screw 470 closely matches the inner diameter of plug 427 and of lever arms 429. Thus, the presence of locking screw 470 prevents lever arms 429 from moving inward toward lumen 424, and therefore maintains projections 431 within the indentation 455 they are mated with. This effectively locks assembly 400 to a particular height, and also secures first and second bodies 410, 440 together and against the distal stem 60 from any further relative movement between one another.

A method of assembling assembly 400 for attachment to a first implant component, such as a distal femoral stem 60, includes a user first inserting plug 427 into recess 441 until projections 431 are disposed within an annular indentation 455 corresponding to a desired height. This holds first and second bodies 410, 440 in such position even without the presence of locking screw 470. If a change in height of assembly 400 is desired, plug 427 can simply be moved to located projections 431 in another indentation 455. This is done without disconnecting first body 410 from second body 440. When the proper height is determined, which can be done while assembly 400 is located on a stem attached to the patient's bone, first body 410 is fixedly connected to second body 440 in the fixedly connected configuration by securing assembly 400 to stem 60 by securing locking screw 470 through lumen 424 in first body 410 and through second body 440 and into a portion of stem 60. This locks first and second bodies 410, 440 together and also locks the adjusted height of assembly 400.

With assembly fixedly connected to distal stem 60, the user can then perform a trialing procedure by installing a trial femoral head on the femoral neck of first body 410, reducing the femoral joint, and assessing the biomechanics of the joint with the implanted assembly 400. If the user determines that the fit of assembly 400 is not appropriate, locking screw 470 can be removed so that the height of assembly 400 can again be adjusted as described above, or one or both of first and second bodies 410, 440 can be replaced and a new, uniquely configured assembly 400 can be assembled and trialed per the method above. Once the proper fit is achieved, the user can select and install a permanent implant that corresponds to the dimensions of the properly fitted assembly 400.

A fifth embodiment in accordance with the present invention is an assembly 400 that is very similar to assembly 400, with like elements numbered similarly. Assembly 500 is shown in FIGS. 25-30 and is also used for trialing in the proximal femur. A detailed discussion of assembly 500 is omitted in favor of a description of those features and methods that differ from assembly 400.

Assembly 500 can be placed into its fixedly connected configuration by inserting a locking screw 570 into lumen 524 of first body 510 and threading it into a distal stem through recess 541 of second body 540. Locking screw 570 also includes an elongated head 571 that extends along a majority of the length of locking screw 570. Head 571 has a non-circular outer circumference that includes opposing circular or cylindrical portions 572 and opposing flat or planar portions 573. Planar portions 573 form reliefs within a cylindrical envelope defined a cylinder including the surfaces of cylindrical portions 572. Locking screw 570 has a narrower threaded portion at its distal end.

Figure 29:
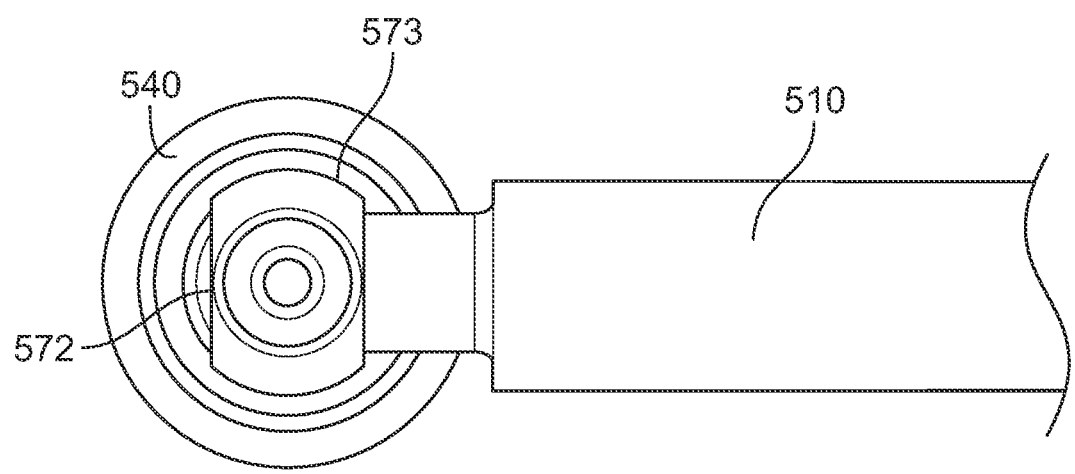

When locking screw 570 is disposed within lumen 524 of plug 527, head 571 can be rotated or placed in a first rotational orientation shown in FIG. 29 in which circular portion 572 is adjacent lever arm 529 and prevents lever arm 529 from moving. This maintains projections 531 within the selected indentation 555. Circular portions 572 are similar to the enlarged diameter of locking screw 470 in this way, in that they closely match the inner diameter of plug 527 and of lever arms 529.

Figure 28:
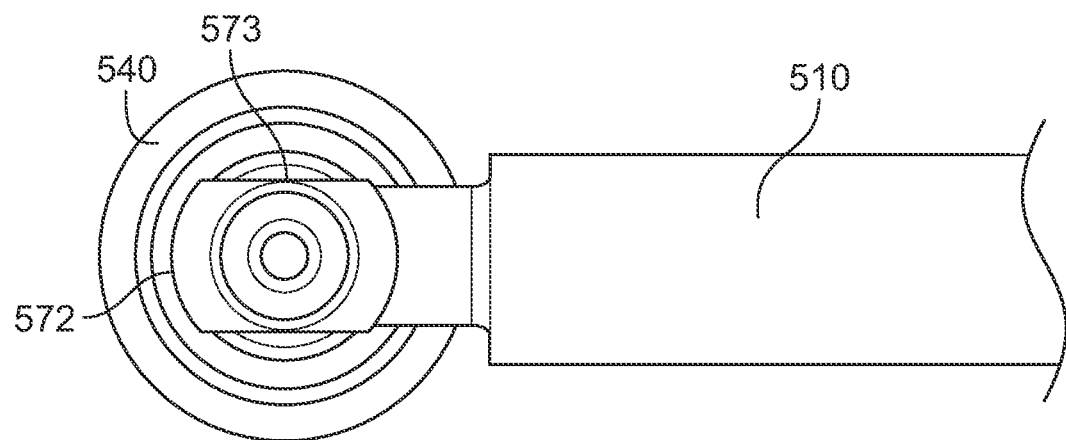
FIGS. 28 and 29 are top views of the trial assembly in accordance with the fifth embodiment in unlocked and locked configurations, respectively.

Head 571 can also be rotated or placed in a second rotational orientation shown in FIG. 28 in which the reliefs at planar portions 573 are adjacent lever arms 529, which allows lever arms 529 and projections 531 to move so that the height of assembly 570 can be adjusted without the need to remove locking screw 570. This allows a user to make adjustments to the modular assembly 500 even after its components are assembled by moving first body 510 along second body 540. Once a desired height is achieved, locking screw 570 can be set to its first rotational orientation to effectively lock assembly 500 to secure first and second bodies 510, 540 together and against the distal stem 60 from any further relative movement between one another.

Figure 30:
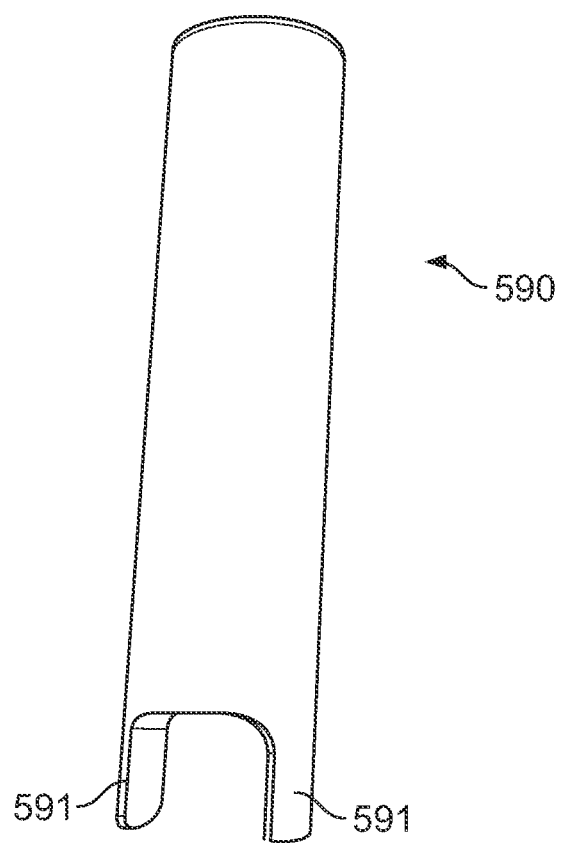
FIG. 30 is a front perspective view of a tool used with the trial assembly in accordance with the fifth embodiment.

A tool 590 is shown in FIG. 30 that can be used to rotate locking screw 570. Ordinarily, a hex driver can be used in a hex-shaped recess in the head of each of the locking screws herein, including locking screw 570. However, when it is desired to control locking screw 570 from a greater height, perhaps due to limitations provided by the anatomy during a surgery, tool 590 includes prongs 591 that fit within reliefs adjacent planar portions 573 of head 571. This allows tool 590 to rotate locking screw 570 when tool 590 is controlled from its proximal end. A kit can be provided for a user that includes assembly 500 along with tool 590.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An assembly for attachment to a first implant component, the assembly having a size and shape of a second implant component to be implanted together with the first implant component, comprising:
    a first body including a plug having a projection;
    a second body including a recess having an internal surface, the internal surface defining multiple indentations; and
    a locking screw wherein in a fixed configuration, the locking screw is secured through the first body and the second body;
    wherein in a temporary configuration, when the plug is disposed within the recess and the projection is disposed at least partially within any one of the indentations, the first and second bodies are removably connected such that the first and second bodies are prevented from separating;
    wherein in the fixed configuration, the first and second bodies are prevented from separating while relative movement is not permitted between the first and second bodies; and
    wherein the first and second bodies are connectable along an axis, and wherein the first and second bodies permit translational movement therebetween along the axis to locate the projection at least partially within any of the indentations without disconnecting the first body from the second body.

2. A system comprising the assembly of claim 1 and the first implant component, and wherein in the fixed configuration, the locking screw is secured into a portion of the first implant component.

3. The assembly of claim 1, wherein each indentation is an annular groove.

4. The assembly of claim 1, wherein the indentations are evenly spaced along the axis.

5. The assembly of claim 1, wherein when assembled together, the first and second bodies correspond to a cone body of a femoral hip assembly as the second implant component.

6. The assembly of claim 5, wherein the first body defines a femoral neck of the cone body, and the second body defines a trunk of the cone body.

7. The assembly of claim 1, wherein the plug of the first body and the recess of the second body are connectable along the axis and each define lumens aligned with the axis in which the locking screw can be disposed.

8. The assembly of claim 7, wherein the plug includes a lever arm on which the projection is disposed.

9. The assembly of claim 8, wherein the locking screw includes a cylindrical head, and wherein, when the first and second bodies are in the fixed configuration, the cylindrical head prevents the lever arm from moving and maintains the projection within one of the indentations.

10. The assembly of claim 8, wherein the locking screw includes a head having a noncircular outer circumference defining a circular portion and a relief, and wherein the head can be placed in a first rotational orientation in which the circular portion is adjacent the lever arm and prevents the lever arm from moving and maintains the projection within one of the indentations, and also in a second rotational orientation in which the relief is adjacent the lever arm and allows the lever arm to move.

11. The assembly of claim 10, wherein when the head of the locking screw is in the second rotational orientation, the first body can be moved along the axis with respect to the second body.

12. A kit comprising:
    the assembly of claim 10; and
    a tool having a prong, wherein the tool can be used to rotate the locking screw with the prong disposed adjacent to the relief.

13. A method of assembling the assembly of claim 1, the method comprising the steps of:
    removably connecting the plug of the first body of the assembly into the recess of the second body of the assembly by locating the projection of the plug within one of the indentations defined in the internal surface of the recess, such that the first and second bodies are prevented from separating; and
    positioning the assembly on the first implant component.

14. An assembly for attachment to a first implant component, the assembly having a size and shape of a second implant component to be implanted together with the first implant component, comprising:
    a first body including a plug having a projection; and
    a second body including a recess having an internal surface, the internal surface defining at least one annular groove;
    wherein in a temporary configuration, when the plug is disposed within the recess and the projection is disposed at least partially within one of the at least one annular groove, the first and second bodies are removably connected such that the first and second bodies are prevented from separating; and
    wherein an external surface of the second body includes an indentation aligned with each of the at least one annular grooves.

15. The assembly of claim 3, wherein the first body includes a second projection, and wherein in the temporary configuration, both of the projections are disposed at least partially within one of the at least one annular grooves.

16. An assembly for attachment to a first implant component, the assembly having a size and shape of a second implant component to be implanted together with the first implant component, comprising:
    a first body including a plug having a projection; and
    a second body including a recess having an internal surface, the internal surface defining at least one indentation;
    wherein in a temporary configuration, when the plug is disposed within the recess and the projection is disposed at least partially within one of the at least one indentations, the first and second bodies are removably connected such that the first and second bodies are prevented from separating; and wherein when assembled together, the first and second bodies correspond to a cone body of a femoral hip assembly as the second implant component, the first body defines a femoral neck of the cone body, and the second body defines a trunk of the cone body, and the first and second bodies are connectable along a first axis, and the femoral neck of the first body extends along a second axis that is angled with respect to the first axis.

17. The assembly of claim 16, wherein:

the trunk defines a maximum outer diameter; and the femoral neck has a conical proximal surface for connecting with a femoral head, the conical proximal surface defining a center point of the femoral neck, and wherein the first body defines an offset distance measured perpendicularly from the first axis to the center point.

18. A modular femoral trialing kit, comprising:

a plurality of the first bodies according to claim 17, each having a different size or shape; and a plurality of the second bodies according to claim 17, each having a different size or shape.

\* \* \* \* \*